(12) United States Patent
Signaevsky et al.

(10) Patent No.: US 11,607,161 B2
(45) Date of Patent: Mar. 21, 2023

(54) BI-DIRECTIONAL NEURON-ELECTRONIC DEVICE INTERFACE STRUCTURES

(71) Applicant: NeuroSilica, Inc., Wilmington, DE (US)

(72) Inventors: Maxim Signaevsky, Brooklyn, NY (US); Igor Yehuda Yaroslavsky, Vancouver (CA)

(73) Assignee: NEUROSILICA, INC., Wilmington, DE (US)

( * ) Notice: Subject to any disclaimer, the term of this patent is extended or adjusted under 35 U.S.C. 154(b) by 496 days.

(21) Appl. No.: 16/815,514

(22) Filed: Mar. 11, 2020

(65) Prior Publication Data

US 2020/0214583 A1 Jul. 9, 2020

Related U.S. Application Data

(63) Continuation of application No. 15/883,793, filed on Jan. 30, 2018, now Pat. No. 10,602,939.

(Continued)

(51) Int. Cl.
*A61B 5/24* (2021.01)
*G06N 3/067* (2006.01)
(Continued)

(52) U.S. Cl.
CPC .............. *A61B 5/24* (2021.01); *A61B 5/7264* (2013.01); *A61N 1/0529* (2013.01); *B06B 1/06* (2013.01);
(Continued)

(58) Field of Classification Search
CPC ... A61B 5/24; A61B 5/7264; A61B 2562/125; A61N 1/0529; B06B 1/06; B06B 1/0688; G06N 3/0675; G06N 3/061; B82Y 30/00
(Continued)

(56) References Cited

U.S. PATENT DOCUMENTS 7,611,628 B1 * 11/2009 Hinds, III ............ B01D 69/141
977/746
10,602,939 B2 * 3/2020 Signaevsky .............. A61B 5/24
(Continued)

FOREIGN PATENT DOCUMENTS

| EP | 1329965 A1 | 5/2002 |
| EP | 1329965 A1 | 7/2003 |
| WO | 2016058097 A1 | 4/2016 |

OTHER PUBLICATIONS

Rowland, N.C. et al., "Merging DBS with viral vector or stem cell implantation: "hybrid" stereotactic surgery as an evolution in the surgical treatment of Parkinson's disease" Molecular Therapy—Methods & Clinical Development (Jan. 2016) pp. 1-6, vol. 3, No. 15051.

(Continued)

*Primary Examiner* — Nathaniel T Woodward
(74) *Attorney, Agent, or Firm* — Tutunjian & Bitetto, P.C.

(57) ABSTRACT

An interface structure for a biological environment including at least one composite electrical impulse generating layer comprising a matrix phase of a piezo polymer material, a first dispersed phase of piezo nanocrystals, and second dispersed phase of carbon nanotubes, the first and second dispersed phase presented through the matrix phase. The piezo polymer material and piezo nanocrystal convert mechanical motion into electrical impulses and accept electrons to charge the composite impulse generating layer. The carbon nanotubes provide pathways for distribution of the electrical impulses to a surface of the composite impulse generating layer contacting the biological environment. The carbon nanotubes further provide for the delivery of the byproducts of the free radical degradation from the biological environment to both piezo-nanocrystals and piezo-polymer.

19 Claims, 15 Drawing Sheets

Related U.S. Application Data

(60) Provisional application No. 62/452,892, filed on Jan. 31, 2017.

(51) Int. Cl.
*A61B 5/00* (2006.01)
*A61N 1/05* (2006.01)
*B06B 1/06* (2006.01)
*G06N 3/06* (2006.01)
*B82Y 30/00* (2011.01)

(52) U.S. Cl.
CPC ......... *B06B 1/0688* (2013.01); *G06N 3/0675* (2013.01); *A61B 2562/125* (2013.01); *B82Y 30/00* (2013.01); *G06N 3/061* (2013.01)

(58) Field of Classification Search
USPC ......................................................... 310/311
See application file for complete search history.

(56) References Cited

U.S. PATENT DOCUMENTS

| | | | |
|---|---|---|---|
| 2009/0299213 A1* | 12/2009 | Patolsky | H01L 29/1606 257/14 |
| 2012/0035440 A1 | 2/2012 | Ferren et al. | |
| 2013/0053934 A1 | 2/2013 | Gluckman et al. | |
| 2013/0338039 A1* | 12/2013 | Mazed | G01N 21/6452 257/253 |
| 2015/0190636 A1* | 7/2015 | Simon | A61N 1/36034 607/72 |
| 2015/0339001 A1 | 11/2015 | Zirkl et al. | |
| 2016/0035956 A1 | 2/2016 | Carroll et al. | |

OTHER PUBLICATIONS

International Search Report and Written Opinion issued in International Application No. PCT/US2018/015953, dated May 24, 2018, pp. 1-7.

European Search Report as issued in 18748436.5 dated Jul. 13, 2020, 7 pages.

\* cited by examiner

BI-DIRECTIONAL NEURON-ELECTRONIC DEVICE INTERFACE STRUCTURES

CROSS REFERENCE TO RELATED APPLICATIONS

This application is a continuation of U.S. application Ser. No. 15/883,793 filed Jan. 30, 2018, entitled "BI-DIRECTIONAL NEURON-ELECTRONIC DEVICE INTERFACE STRUCTURES", incorporated herein in its entirety by reference, which application claims the benefit of U.S. Provisional Application No. 62/452,892 filed Jan. 31, 2017, entitled "A SUSTAINABLE SELF-POWERED BI-DIRECTIONAL NEURON-SILICA INTERFACE TECHNOLOGY", incorporated herein in its entirety by reference.

BACKGROUND

Technical Field

The present invention generally relates to interfaces with biological environments that can create as well as transmit electrical impulses, as well as receive electrical impulses from the biological environment, and more particularly to interfaces composed of piezoelectric materials and nano structures.

Description of the Related Art

The interaction between the biological systems and mechanical or electrical machines has been in the interest of mankind for centuries. With the discovery of electricity and electric properties of nerves and muscles, there had been numerous attempts to make a functional interface between the body and the machine or an artificial/prosthetic device.

Deep brain stimulation (DBS) is an approach to address the issue of the substitution of the loss of function in neurological diseases such as Parkinson's disease. Current DBS devices are electrical devices consisting of 2-4 electrodes implanted in the brain and wired to a portable battery-powered device usually implanted in the chest area. The battery is placed under the skin of the chest. The routine battery change is every 5+ years. Maintenance, replacement, and possible hardware malfunction are associated with the risk of medical complications.

SUMMARY

The methods and structures described herein can provide a neuron-computer bi-directional interface material. The interface material layer include of a sustainable self-powered composite polymer with embedded nano-crystals and carbon nano-tubes for integration in a neuron-glial network. The neuron-computer bi-directional interface material can be used as a stimulator of excitable tissue, and can be used as interface for functional prosthetics.

In accordance with an embodiment of the present invention, an interface structure is provided for transmitting to and receiving electrical impulses from a biological environment. In some embodiments, the interface structure may include at least one composite impulse generating layer comprising a matrix phase of a piezo polymer material, a first dispersed phase of piezo nanocrystals, and second dispersed phase of carbon nanotubes, the first and second dispersed phase presented through the matrix phase, wherein the piezo polymer material and piezo nanocrystal convert mechanical motion into electrical impulses and accept electrons to charge the composite impulse generating layer, and the carbon nanotubes provide pathways for distribution of the electrical impulses to a surface of the composite impulse generating layer contacting the biological environment, and the delivery of free radicals from the biological environment to at least the piezo nanocrystals, or piezo elements including piezo nanocrystals and piezo polymer.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

a dielectric polymer layer; and at least one biological environment interface layer having a grid geometry, in accordance with one embodiment of the present disclosure.

Figure 7:
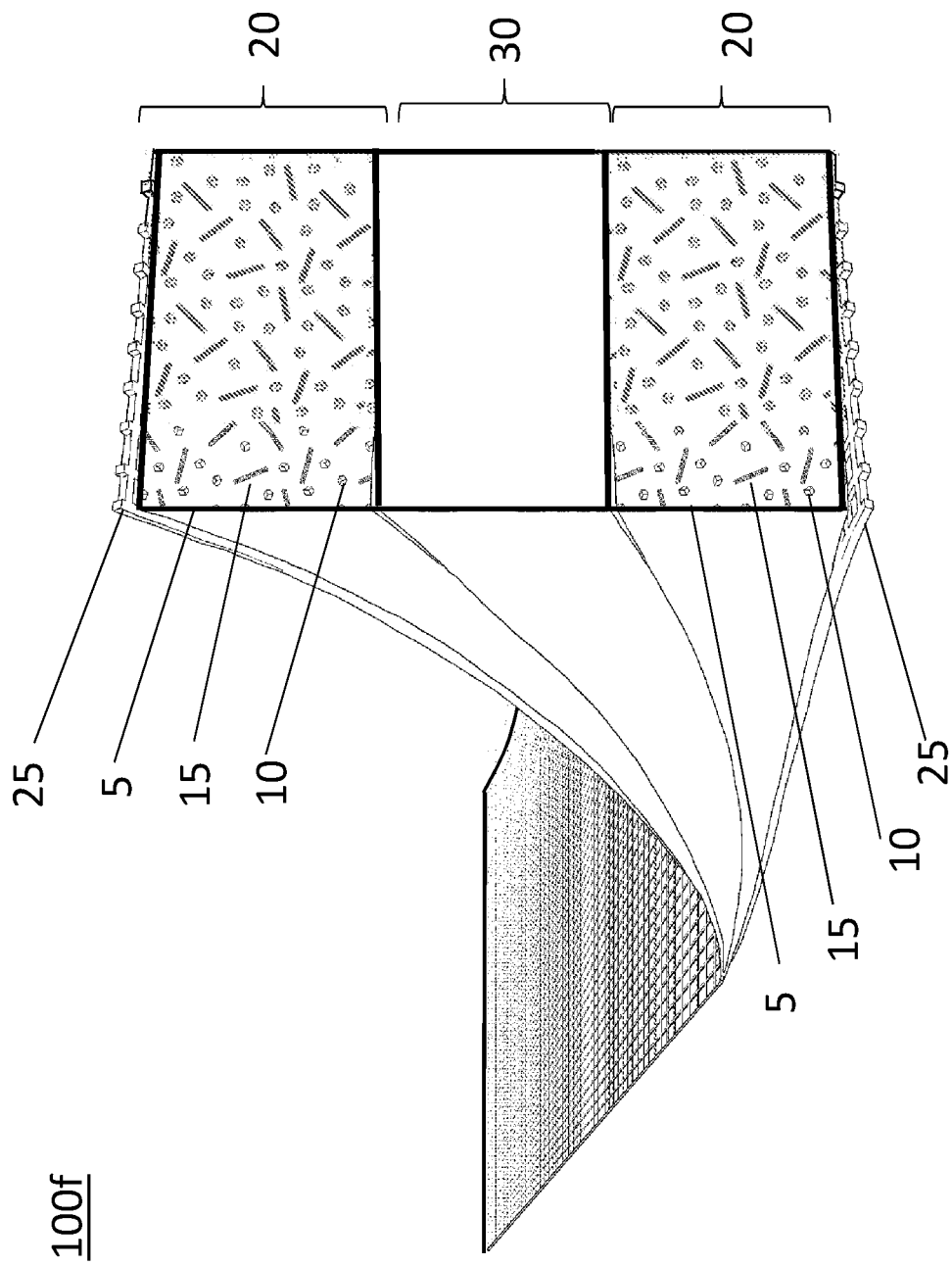

FIG. 7 is a perspective view of a neuron-computer bi-directional interface structure having a film and ribbon form factor, in which the interface structure is a multi-layered structure including a dielectric polymer layer positioned between two composite electrical impulse generating layers; and at least one biological environmental interface layer having a grid geometry, in accordance with one embodiment of the present disclosure.

Figure 8:
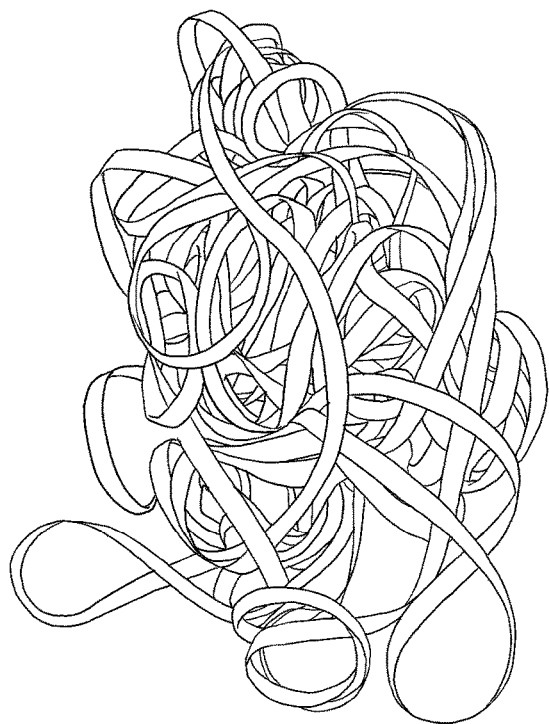

FIG. 8 is a perspective view of a neuron-computer bi-directional interface structure having a film and ribbon form factor in the geometry of a haphazard ribbon.

Figure 9:
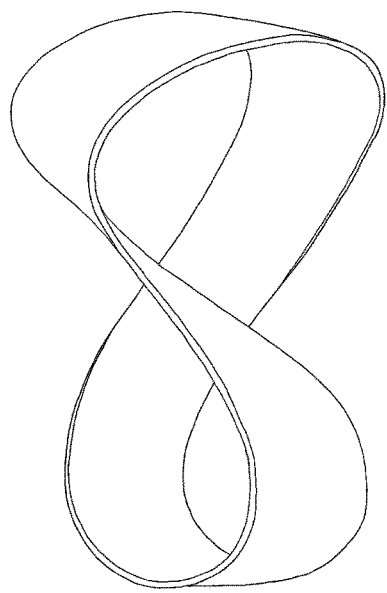

FIG. 9 is a perspective view of a neuron-computer bi-directional interface structure having a film and ribbon form factor in the geometry of a mobious loop.

Figure 10:
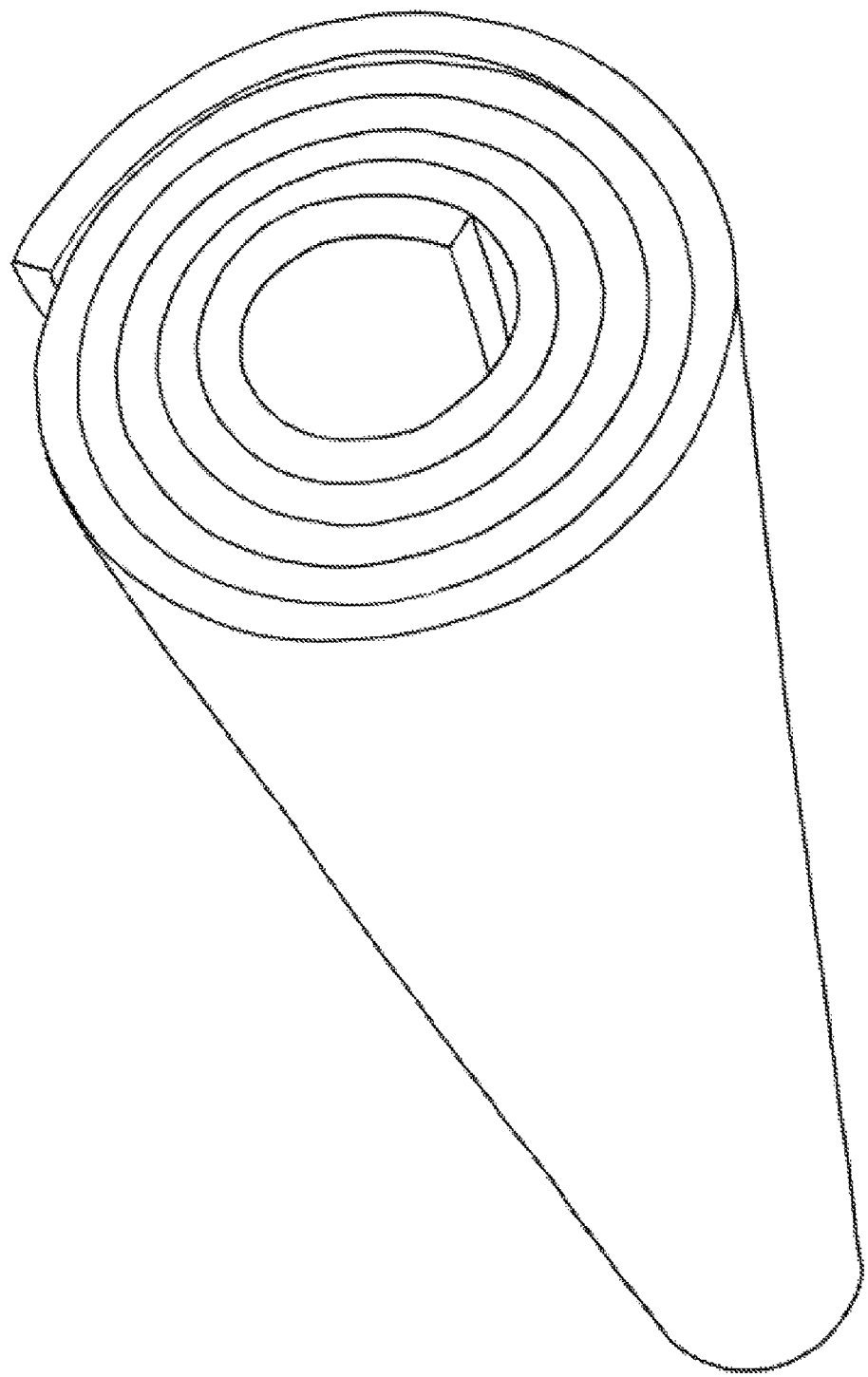

FIG. 10 is a perspective view of a neuron-computer bi-directional interface structure having a film and ribbon form factor in the geometry of a coil.

Figure 11:
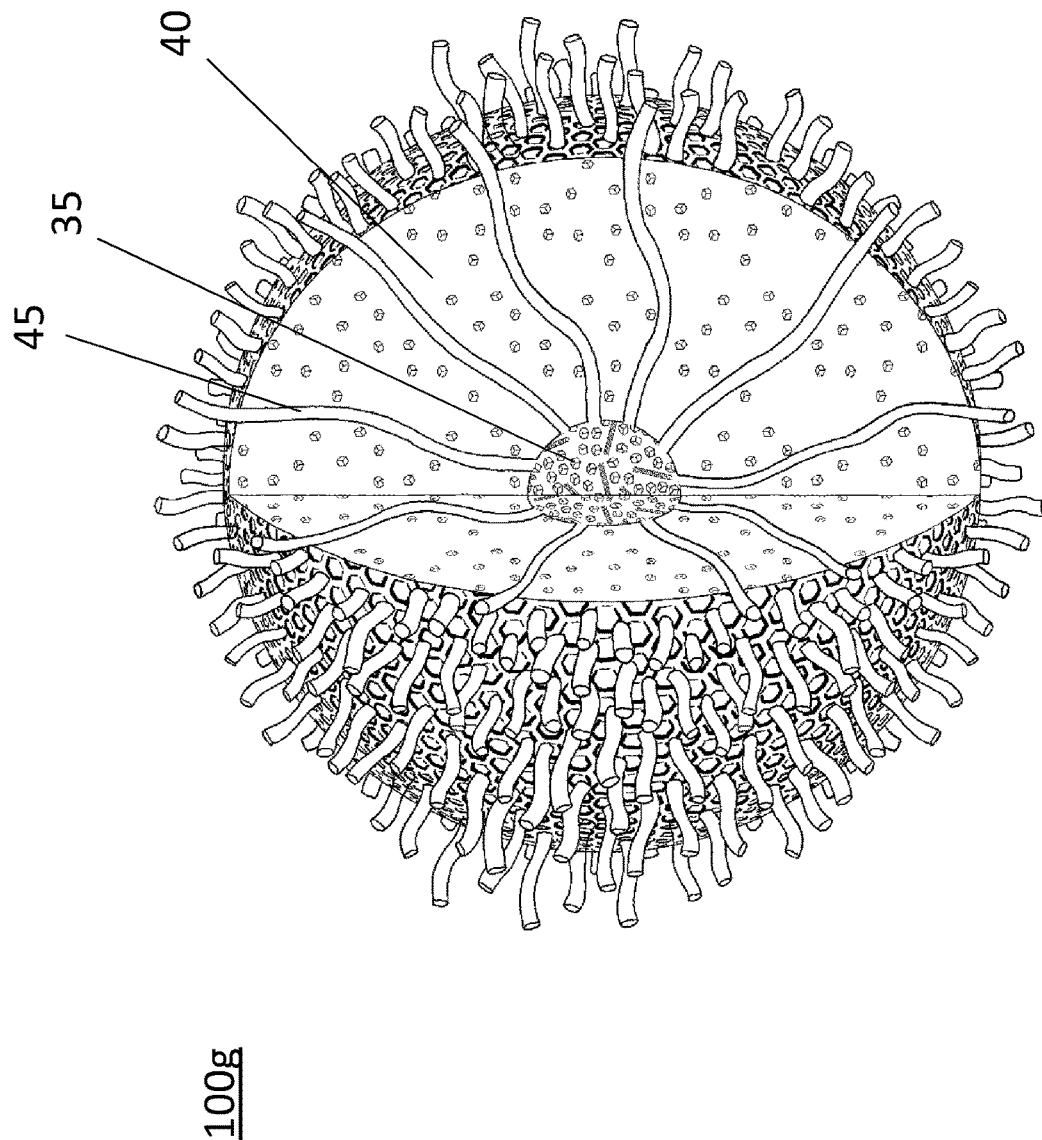

FIG. 11 is a perspective view of a neuron-computer bi-directional interface structure having a three dimensional form factor in the shape of a sphere having a plurality of spikes/columns extending from the outer surface of the sphere.

Figure 12:
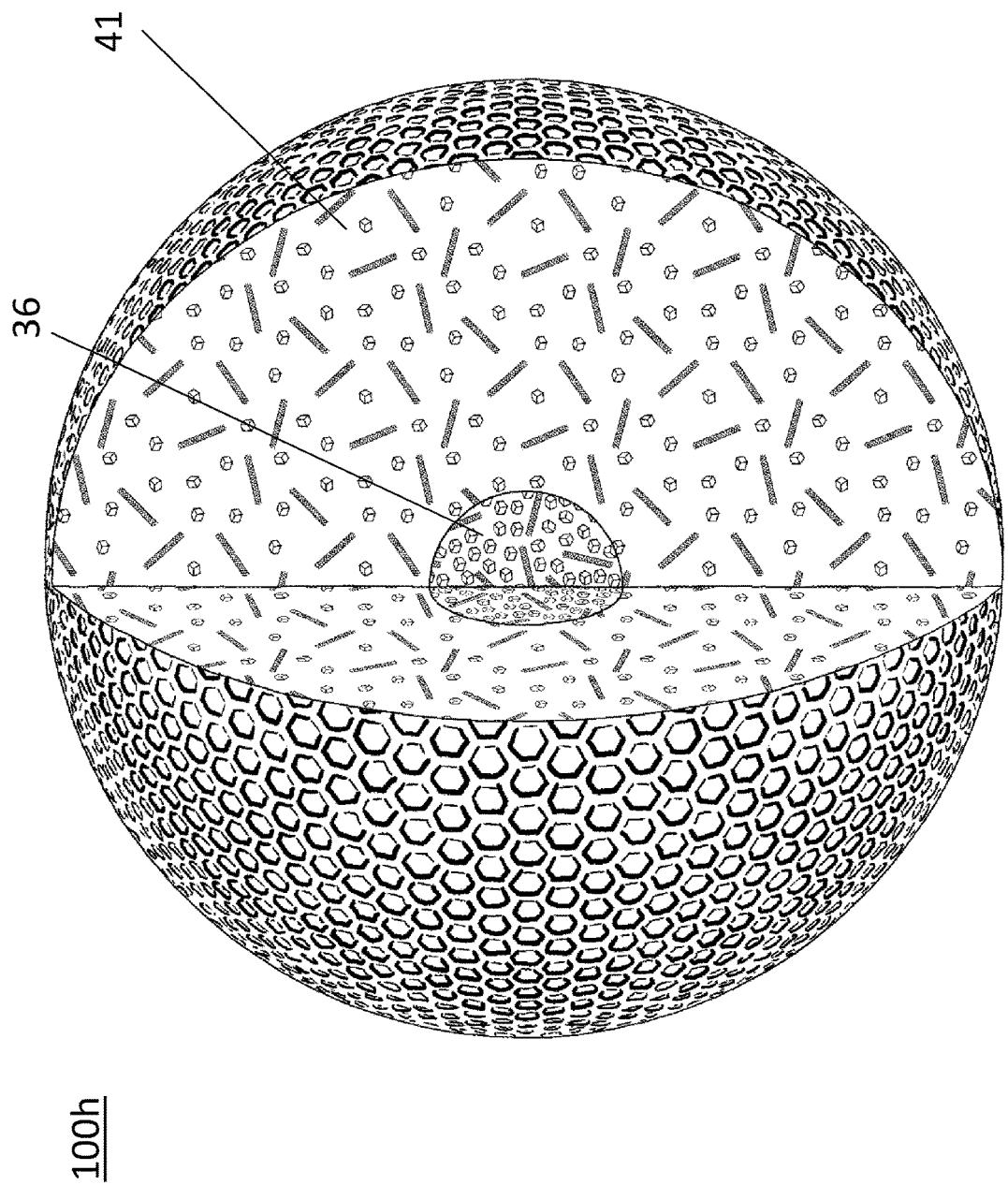

FIG. 12 is a perspective view of a neuron-computer bi-directional interface structure having a three dimensional form factor in the shape of a sphere having a nucleus present within an outer sphere.

Figure 13:
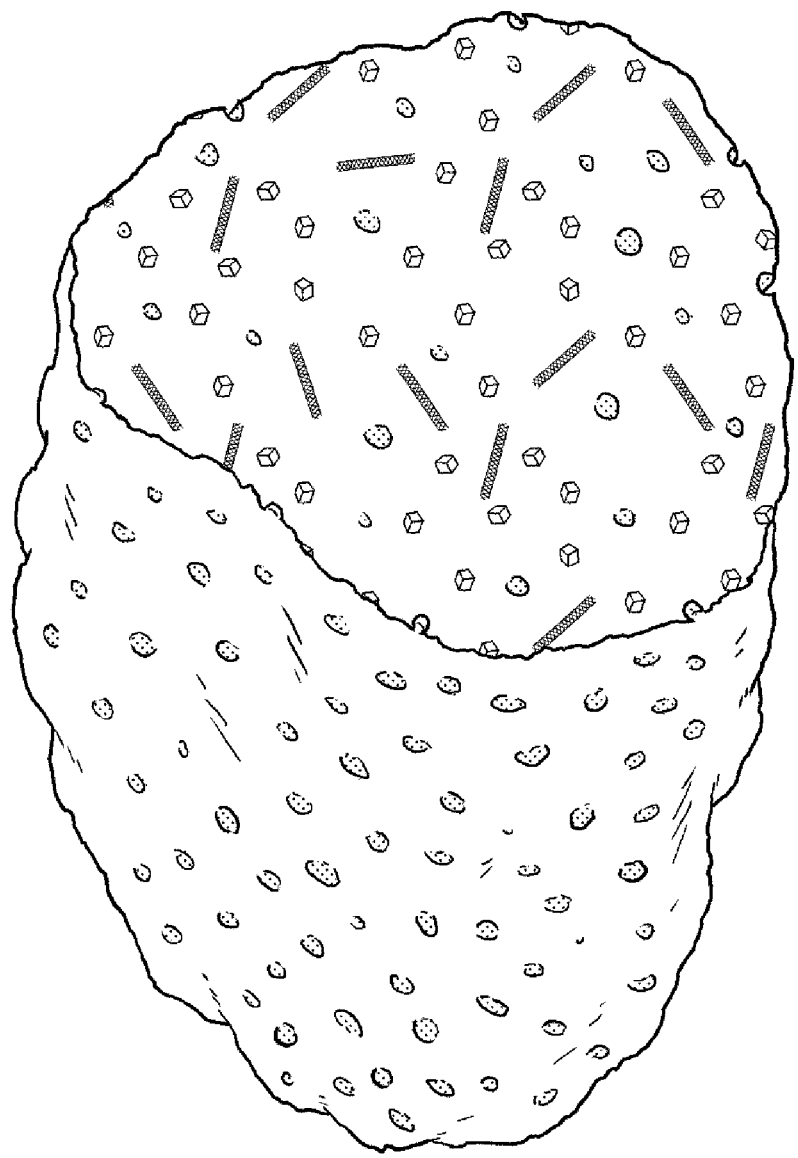

FIG. 13 is a perspective view of a neuron-computer bi-directional interface structure having a three dimensional form factor in the shape of a sponge, in accordance with one embodiment of the present disclosure.

Figure 14:
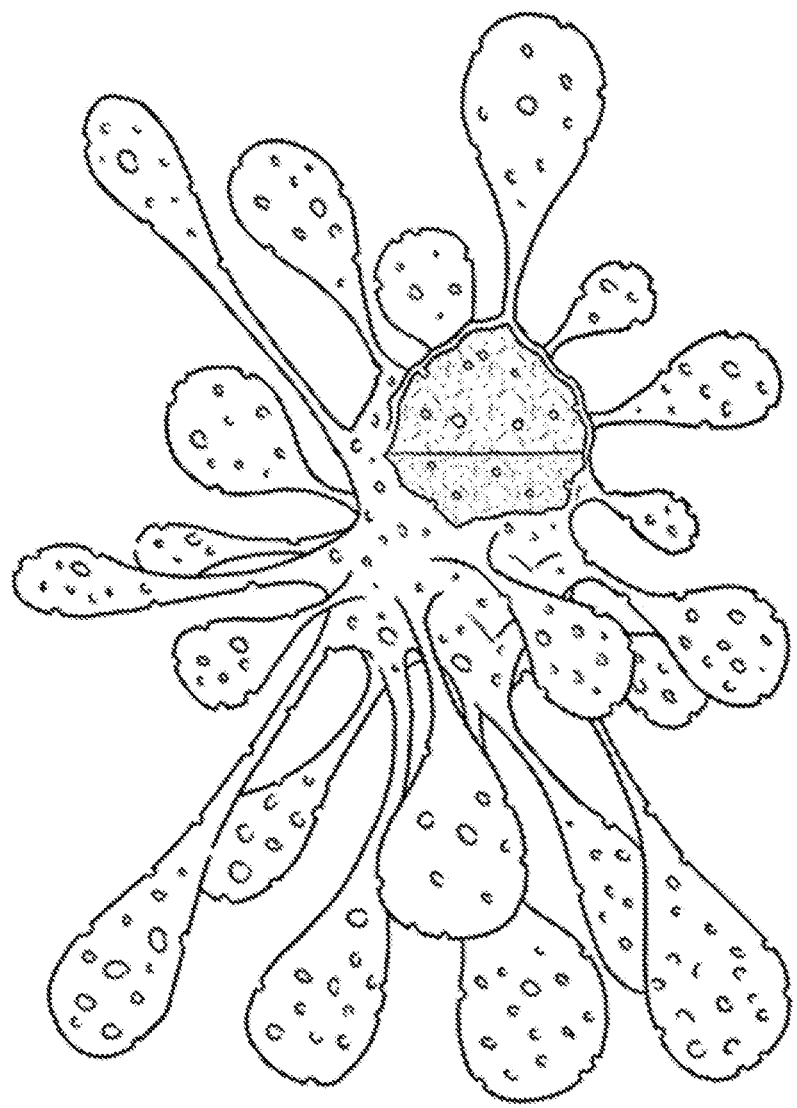

FIG. 14 is a perspective view of a neuron-computer bi-directional interface structure having a three dimensional form factor in the three dimensional blot, in accordance with one embodiment of the present disclosure.

Figure 15:
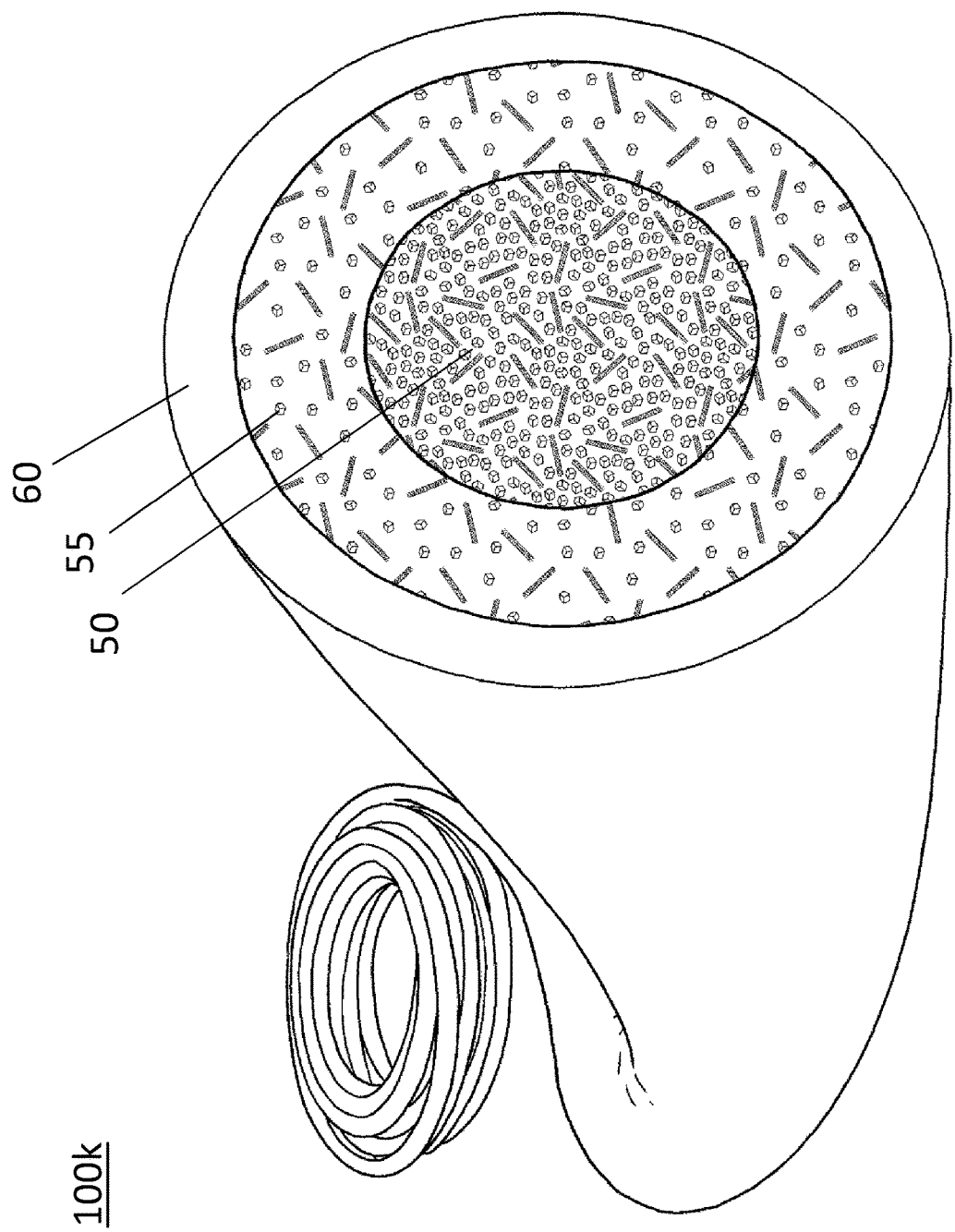

FIG. 15 is a perspective view of a neuron-computer bi-directional interface structure having a three dimensional form factor having a wire type geometry, in accordance with one embodiment of the present disclosure.

Figure 16:
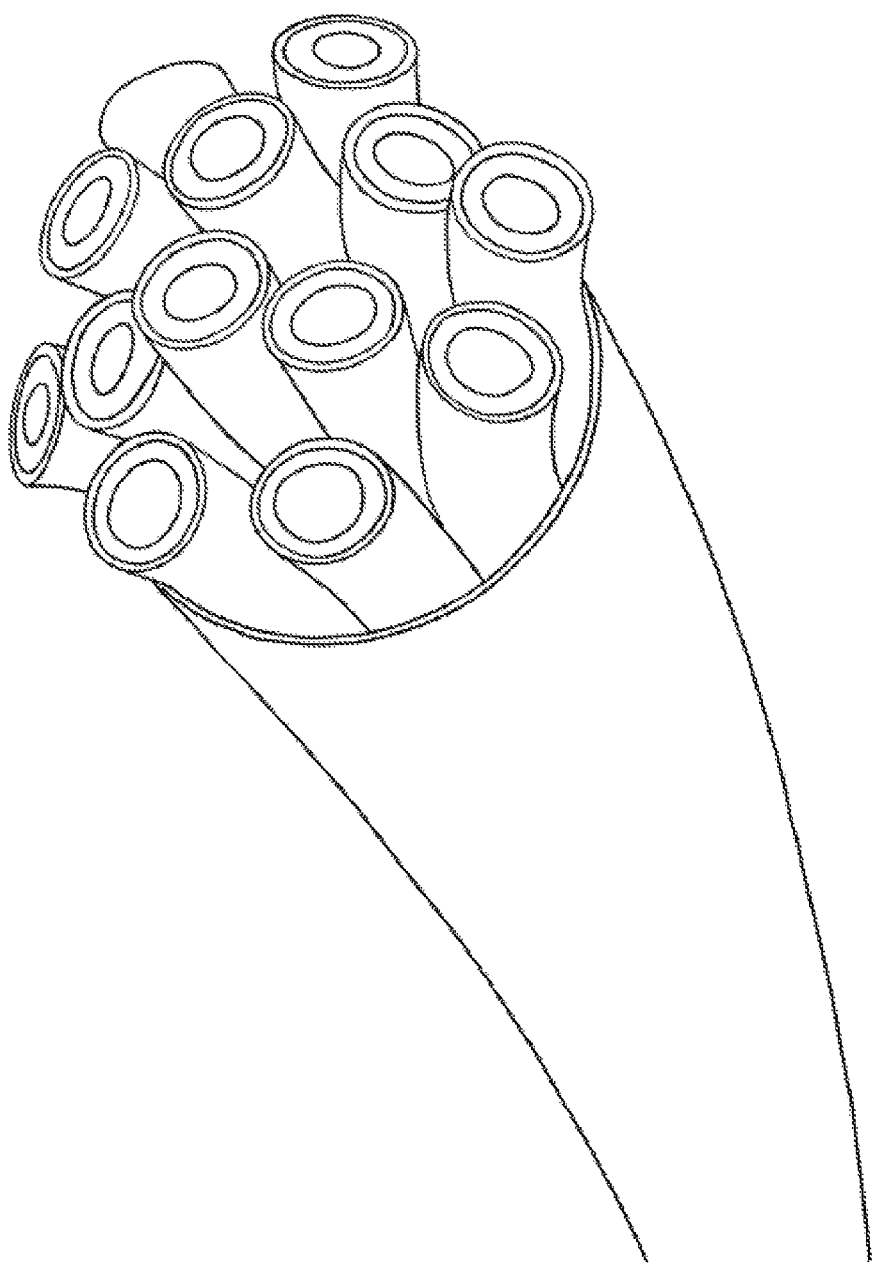

FIG. 16 is a perspective view of a neuron-computer bi-directional interface structure having a three dimensional form factor having a geometry including multiple wires, in accordance with one embodiment of the present disclosure.

DETAILED DESCRIPTION

Detailed embodiments of the claimed structures and materials are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment. For purposes of the description hereinafter, the terms "upper", "over", "overlying", "lower", "under", "underlying", "right", "left", "vertical", "horizontal", "top", "bottom", and derivatives thereof shall relate to the embodiments of the disclosure, as it is oriented in the drawing figures. The term "positioned on" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, insulating or semiconductor layers at the interface of the two elements.

The methods and structures described herein can provide a neuron-computer bi-directional interface material that can include of a self-powered composite polymer with embedded nano-crystals and carbon nano-tubes. The neuron-computer bi-directional interface material can be used as a stimulator of excitable tissue, e.g., brain tissue, spinal cord tissue, peripheral nerves, skeletal and heart muscles, etc., and can be used as interface for functional prosthetics and brain computer interface devices, including but not limited to, biorobotic, exoskeletons, and implantable devices.

In some embodiments, the self-powered composite polymer provides that the interface material be a flexible, as well as stretchable, piezoelectric energy harvesters that can harvest minute biomechanical motions in human body and transduce it into electric impulses/current. Such technology can be further used in self-powered sensitive piezoelectric medical devices. More specifically, in some embodiments, to provide the self-powered aspect of the composite structure, electric impulses are generated in the composite polymer with embedded nano-piezo-elements through the transduction of mechanical movement into electromotive force (EMF). The EMF will generate an electric current utilized by adjacent neurons to facilitate cell membrane depolarization and further propagation of the action potential along the neuronal/axonal network.

The conversion of mechanical movement into electromotive force (EMF) results from piezo-electric effects produced from both a piezo polymer material that provides the matrix material for an interface structure for transmitting and receiving electrical impulses from a biological environment, and piezo nano crystals that are a dispersed phase that can be present throughout an entirety of the matrix material. Piezo-electric effects, i.e., piezo-electricity, is based on the ability of a material, e.g., crystal, to generate an electrical charge when mechanically loaded with pressure or tension, which is called the direct piezo effect.

A piezoelectric polymer is a material having piezoelectricity, i.e., the ability of material, which is the property that the polarization of a material change by applying stress and/or strain generated by changing polarization). The piezoelectric polymer provides the matrix of a composite structure. A composite is a material composed of two or more distinct phases, e.g., matrix phase and dispersed phase, and having bulk properties different from those of any of the constituents by themselves. As used herein, the term "matrix phase" denotes the phase of the composite that is present in a majority of the composite, and contains the dispersed phase, and shares a load with it. In the present case, the matrix phase may be provided by a polymer.

The word "polymer" can be defined as a material made out of a large number of repeating units which are linked to each other through chemical bonding. A single polymer molecule may contain millions of small molecules or repeating units which are called monomers. Polymers are very large molecules having high molecular weights. Monomers should have a double bond or at least two functional groups in order to be arranged as a polymer. This double bond or two functional groups help the monomer to attach two more monomers, and these attached monomers also have functional groups to attract more monomers. A polymer is made in this way and this process is known as polymerization. The result of polymerization is a macromolecule or a polymer chain. These polymer chains can be arranged in different ways to make the molecular structure of a polymer. The arrangement can be amorphous or crystalline. The main difference between amorphous and crystalline polymers is their molecular arrangement. Amorphous polymers have no particular arrangement or a pattern whereas crystalline polymers are well arranged molecular structures. Further details on the piezoelectric polymer are provided below.

As noted above, piezoelectric electric generation, i.e., electric impulses are not only generated by the piezoelectric polymer, but are also generated by piezo nanocrystals that are present as one dispersed phase of the composite. Crystalline solids or crystals, e.g., the piezo nanocrystals, have ordered structures and symmetry. The atoms, molecules, or ions in crystals are arranged in a particular manner; thus, have a long range order. In crystalline solids, there is a regular, repeating pattern; thus, we can identify a repeating unit.

In some embodiments, the piezo nanocrystal is provided by a ceramic composition. Ceramics exhibiting piezo-electric properties can belong to the group of ferroelectric materials. One family of ceramic nanocrystals exhibiting piezo-electric properties include lead zirconate titanate (PZT); in which the members of this family consist of mixed crystals of lead zirconate ($PbZrO_3$) and lead titanate ($PbTiO_3$). Piezo-ceramic components have a polycrystalline structure comprising numerous crystallites (domains) each of which consists of a plurality of elementary cells. The elementary cells of these ferroelectric ceramics exhibit the perovskite crystal structure, which can generally be described by the structural formula $A^{2+}B^{4+}O_3^{2-}$. The piezo nanocrystals may also include niobium (Nb) based crystals.

Similar to the piezoelectric polymer, the piezo electric nanocrystals generate an electrical charge when mechanically loaded with pressure or tension, which is referred to above as the piezo effect. The piezo nanocrystals are of a nanoscale. "Nanoscale" denotes that the piezo nanocrystals have a cross-section width that is less than 500 nm. In some examples, the piezo nanocrystals have a cross-sectional width ranging from 20 nm to 100 nm.

The piezo nanocrystals provide one dispersed phase of the composite, in which the matrix phase of the composite is provided by a piezo polymeric material. As used herein, the term "dispersed phase" denotes a second phase (or phases) that is embedded in the matrix phase of the composite. The dispersed phase may be present throughout an entirety of the material that provides the matrix.

The composite also includes a second dispersed phase of carbon nanotubes. The carbon nanotubes provide pathways for distribution of the electrical impulses to a surface of the composite impulse generating layer contacting the biological environment, and the delivery of free radicals from the biological environment to at least the piezo nanocrystals. "Nanotube" as used herein is meant to denote one form of nanostructure having an aspect ratio of length to width greater than 10. The term "nanotube" includes single wall and multi-wall nanotubes unless specifically specified as distinct. In one embodiment, a carbon nanotube is at least one graphene layer wrapped into a cylinder. In one embodiment, a single wall carbon nanotube is a graphene rolled up into a seamless cylinder with diameter of the order of a nanometer. A multi-wall carbon nanotube is a plurality of graphene sheets rolled up into a seamless cylinder with diameter of the order of a nanometer.

The composite of the piezo polymer, the piezo nanocrystal and the carbon nanotubes can provide an interface structure for transmitting and receiving electrical impulses from a biological environment. For example, the electric current produced by the composite may be utilized by adjacent neurons to facilitate cell membrane depolarization and further propagation of the action potential along the neuronal/axonal network. Compared to conventional neuronal tissue stimulating technologies the operating power of devices employing the composite material of the piezo polymer, the piezo nanocrystal and the carbon nanotubes can be lower owing to enhanced biocompatibility and shape of the polymer electrode. Implantable devices built on the proposed technology can be suitable for clinical applications that include, but are not limited to, deep brain stimulation for neurogenerative diseases, e.g., Parkinson's disease; neuromodulation for major depression; urinary incontinence; neuro-trauma; essential tremor; epilepsy; and combinations thereof. The methods and structures of the present disclosure are now described with greater detail with reference to FIGS. 1-16.

Figure 1:
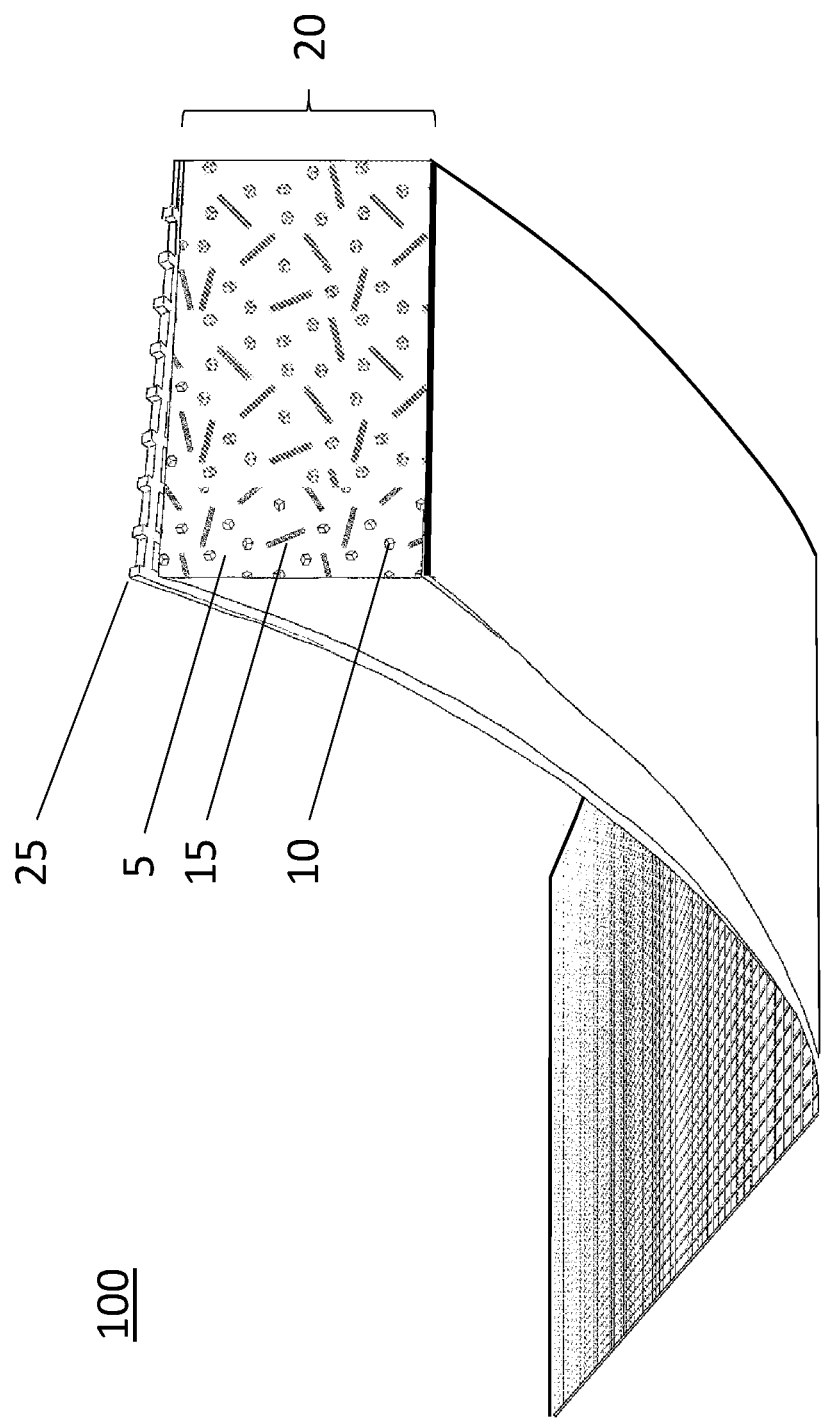
FIG. 1 is a perspective view of a neuron-computer bi-directional interface structure having a film and ribbon form factor, in which the interface structure is a multi-layered structure including a composite layer of a piezo polymeric matrix material, a first dispersed phase of piezo nanocrystal material, and a second dispersed phase of carbon nanotubes, and at least one biological environment interface layer having a grid geometry, in accordance with one embodiment of the present disclosure.

FIG. 1 depicts one embodiment of a neuron-computer bi-directional interface structure 100 having a film and ribbon form factor, in which the interface structure is a multi-layered structure including a composite layer 20 of a piezo polymeric matrix material 5, a first dispersed phase of piezo nanocrystal material 10, and a second dispersed phase of carbon nanotubes 15, and at least one biological environment interface layer 25 having a grid geometry.

The composite layer 20 may be referred to a composite electrical impulse generating layer that includes a matrix phase of a piezo polymer material 5, a first dispersed phase of piezo nanocrystals 10, and second dispersed phase of carbon nanotubes 15, in which the first and second dispersed phases are presented throughout the matrix phase. As illustrated in FIG. 1, the first dispersed phase of piezo nanocrystals 10 and the second dispersed phase of the carbon nanotubes 15 may be uniformly distributed throughout the entirety of the matrix of the piezo polymer material 5. The composite electrical impulse generating layer 20 is a flexible and stretchable piezoelectric generator that can provide a self-powered energy system for various applications.

The piezo polymer material 5 and piezo nanocrystal 10 convert mechanical motion into electrical impulses and accept electrons to charge the composite electrical impulse generating layer 20. In some embodiments, the addition of the first dispersed phase of the piezoelectric nano-material 10 in the form of nano-wires or nano-crystals into the matrix phase of the piezo polymer material 5 provides piezoelectric composition that can generate a high output power with higher efficiency when compared with other piezoelectric nanostructures. For example, nanowires of $Pb(Mg_{1/3}Nb_{2/3})O_3$—$PbTiO_3$ (PMN-PT) is one composition of piezo nanocrystals 10 that can dispersed throughout a matrix of a piezo polymer material 5 that is β-phase polyvinylidene fluoride trifluoroethylene (PVDF-TrFE), wherein the piezoelectric coupling coefficient (d33) of PMN-PT nanowires is about 371 pm/V, which is over 13 times higher than that of BaTiO$_3$ nanoparticles and 90 times higher than that of NaNbO$_3$ nanowires, which are approximately 28 and 4 pm/V, respectively. It is noted that this example is intended to be illustrative only, and not intended to limit the present invention. Other compositions are equally suitable for the piezo polymer 5 and the piezo nanocrystals 10.

For example, the piezo polymer 5 that provides the matrix for the composite may be polyvinylidene fluoride trifluoroethylene (PVDF-TrFE), which is a copolymer of PVDF. Polyvinylidene fluoride trifluoroethylene (PVDF-TrFE) can crystallize into β-phase directly from melt. In some embodiments, β-phase is thermodynamically favored for piezoeffect. In other examples, the piezo polymer material may have a composition that is selected from the group consisting of polyvinylidene flouride (PVDF), polyvinylidene fluoride (PVDF) copolymer with triflourethylene (TrFE), polyvinylidene fluoride (PVDF) copolymer with tetrafluorethylene (TFE), polyvinylidene fluoride (PVDF) copolymer with tetrafluorethylene (TFE) and triflourethylene (TrFE), nylon 11, poly(vinylidenecyanide vinylacetate), and combinations thereof.

In some embodiments, the piezo nanocrystal 10 can be composed of a piezo ceramic material. For example, the piezo ceramic material that provides the piezo nanocrystal 10 may have a composition selected from the group consisting of lead zirconate (PbZrO$_3$), lead titanate (PbTiO$_3$), and combinations thereof.

In one example, the material composition of the piezo nanocrystal 10 that is employed in the composite electrical impulse generating layer 20 is a single-crystal piezoelectric (1-χ)PbZn$_{1/3}$Nb$_{2/3}$O$_{3-χ}$PbTiO$_3$ (PZNT) (further PMN-PT), which has a piezo-electric coupling coefficient (d33) up to 2500 pm/V, which is higher than that of conventional piezo-ceramics. For example, the piezoelectric coupling coefficient (d33) of single-crystal bulk PMN-PT is about 30 times higher than that of BaTiO$_3$, which is approximately 85.3 pm/V, and almost 4 times higher than that of PZT bulk material.

In another example, the material of the piezo nanocrystal 10 is Li-doped (K, Na)NbO$_3$ as a ceramic piezoelectric crystalline component. In yet another example, which may be suitable for long-term biocompatibility, lead free materials may be preferred. For example, the piezo nanocrystal 10 can be Ba(Ce$_x$Ti$_{1-x}$O$_3$), which is a mixture of Cerium-Barium Titanate (C-BT) with (0.94(Bi$_{0.5}$Na$_{0.5}$TiO$_3$)+0.06 (BaTiO$_3$)) as a solid solution.

The first dispersed phase of piezo nanocrystals 10 may have a nanowire-type geometry, and in some instances can have a substantially spherical geometry. In the instances, in which the piezo nanocrystals 10 have a nanowire-type geometry, the piezo nanocrystals 10 have a cross-sectional width ranging from 20 nm to 100 nm, and the length of the piezo nanocrystals 10 can range from 100 nm to 500 nm. The dimensions of the piezo nanocrystals 10 are provided for illustrative purposes only, and are not intended to limit the present disclosure to this example.

Still referring to FIG. 1, the composite electrical impulse generating layer 20 also includes a second dispersed phase of nanotubes, i.e., carbon nanotubes 15. The carbon nanotubes 15 provide pathways for distribution of the electrical impulses to a surface of the composite impulse generating layer contacting the biological environment. The carbon nanotubes 15 further provide for the delivery of the byproducts of the free radical degradation from the biological environment to both piezo-nanocrystals and piezo-polymer.

Carbon nanotubes (CNT) 15 are cylindrical structures made of carbon with unique mechanical and electronic properties. Carbon nanotubes (CNTs) 15 are rolled up sheets of hexagonally ordered carbon atoms, giving tubes with diameters on the order of a few nanometers and lengths typically in the micrometer range. They may be single-walled or multiwalled (SWCNTs and MWCNTs respectively), and can be electrically conducting or semiconducting depending upon the orientation of the carbon lattice with respect to the tube axis (known as chirality in this context). In some embodiments, the carbon nanotubes (CNTs) 15 are designed to haphazardly penetrate polymer matrix, i.e., piezo polymer material 5. The function of the carbon nanotubes (CNTs) 15 are to collect, conduct, and accept electrons and toxic free oxygen radicals in intercellular space [$O^{3-}$+ $C+e=CO_2$], including those generated as a result of electric impulses delivery.

In one embodiment, the carbon nanotubes 15 may have a high purity on the order of about 95% to about 99% carbon. In an even further embodiment, the carbon nanotubes 15 have a high purity on the order of about 99% or greater. In one embodiment, the carbon nanotubes 15 may be provided by laser vaporization. In one embodiment, the single wall carbon nanotubes 15 are formed using laser vaporization in combination with a catalyst, such as a metal catalyst. In one embodiment, the catalyst is supported on a substrate, such as a graphite substrate, or the catalyst may be floating metal catalyst particles. In one embodiment, the metal catalyst may be composed of Fe, Ni, Co, Rh, Y or alloys and combinations thereof.

The carbon nanotubes 15 comprise a majority of carbon typically being of high purity. In other examples, the carbon nanotubes include a carbon content ranging from being greater than 50%, wherein a purification process is utilized to provide carbon nanotubes having of high purity, such as greater than 90% carbon. In one embodiment, the carbon nanotubes may be purified by a process that includes an acid treatment followed by an oxidation. In one embodiment, the acid treatment may include treatment and oxidation steps are provided by a dilute HNO$_3$ reflux/air oxidation procedure.

Other methods of forming the carbon nanotubes may also be employed, such as chemical vapor deposition (CVD). In another embodiment, the carbon nanotubes may be multi-walled.

The diameter of a single wall carbon nanotube 15 may range from about 1 nanometer to about 400 nanometers. In another embodiment, the diameter of a single wall carbon nanotube 15 may range from about 1.2 nanometers to about 1.6 nanometers. In one embodiment, the nanotubes 15 used in accordance with the present invention have an aspect ratio of length to diameter on the order of approximately 200:1 or greater. For example, the length of the carbon nanotubes (CNTs) 15 may be as great as 1 mm.

In some embodiments, the composite electrical impulse generating layer 20 may include the piezo polymeric material 5 in an amount ranging from 70 wt. % to 84.9 wt. %; piezo nanocrystals 10 in an amount ranging from 15 wt. % to 30 wt. %; and carbon nanotubes 15 in an amount ranging from 0.1 wt. % to 1 wt. %. In one example, the piezo polymeric material 5 is present in the composite electrical impulse generating layer 20 in an amount equal to 79.5 wt. %; the piezo crystal 10 are present in the composite electrical impulse generating layer 20 in an amount equal to 20 wt. % and the carbon nanotubes 15 are present in an amount that is equal to 0.5 wt. %.

In some embodiments, the thickness of the composite impulse generating layer 20 may range from 40 μm to 300

μm. In one example, the thickness of the composite impulse generating layer 20 is equal to 100 μm.

In one example, the composite impulse generating layer 20 may have a piezo-electric coefficient d33 ranging from 30-350 pC/N, and a polarization ranging from 2500-10000 mC/cm$^2$.

Referring to FIG. 1, the interface structure 100 may further include at least one biological environment interface layer 25 is in contact with the surface of the composite impulse generating layer 20 to provide a multi-layered interface structure, the electrical impulses reaching the surface of the composite impulse generated layer 20 transmitted by biological environmental interface layer to stimulate cells in the biological environment. The biological environmental interface layer 25 may also be referred to as an outer layer.

In some embodiments, the at least one biological environment interface layer 25 is for harvesting and the distribution of electrical impulses. In some examples, the at least one biological environment interface layer 25 may include a metal containing layer, which may be gold (Au). The at least one biological environment interface layer 25 is not limited to gold (Au). For example, in some other embodiments, the at least one biological environmental interface layer is provided by a metal composition selected from the group consisting of silver, platinum, iridium, and combinations thereof including combinations with gold. In some embodiments, the metal coating for providing the biological environmental interface 25 can be provided by plating, e.g., electroplating and/or electroless plating, physical vapor deposition (PVD), e.g., sputtering and/or chemical vapor deposition (CVD) technology.

In some embodiments, the biological environmental interface 25 is in a form of a perforated foil or a mesh. In the metal layer for the biological environmental interface 25, the spaces are formed in predetermined patterns that allow for the metal foil or mesh to flex without buckling. The metal between the spaces defines a plurality of discrete electrodes on the metal foil when the foil is cut and formed into a structure. This can allow for the creation and concentration of electrical impulses in certain points of the biological environmental interface 25.

The metal layer for the biological environmental interface 25 may have a thickness ranging from 8 μm to 12 μm. In one example, the metal layer for the biological environmental interface 25 may have a thickness of 10 μm.

In other embodiments, the biological environmental interface 25 may be provided metal nano-particles embedded in the polymer, e.g. mixture of piezo-polymer and dielectric polymers; and/or a random distribution of nano metal dots and/or micro metal dots on the surface of the film/ribbon geometry form factor for the interface structure 100.

In some other embodiments, the biological environmental interface layer 25 may also be provided by a mixture of piezo polymeric material and dielectric polymeric material. The piezo polymeric material of the biological environmental interface layer 25 may be similar in composition to the piezo polymer 5 of the composite electrical impulse generating layer 20. For example, the piezo polymer for the biological environmental interface layer 25 may be polyvinylidene fluoride trifluoroethylene (PVDF-TrFE). In some embodiments, the piezo polymer material may be mixed with a dielectric polymer, such as polydimethylsiloxane (PDMS). For example, the mixture of piezo polymer and dielectric polymer for providing a biological environmental interface layer 25 may include 10 wt. % to 30 wt. % piezo polymer, and 70 wt. % to 90 wt. % dielectric polymer. In some instances the mixture of piezo polymer and dielectric polymer for the biological interface layer 25 may also include a dispersed phase of carbon nanotubes. In one embodiment, the carbon nanotubes may be present in the piezo polymer and dielectric polymer composition in an amount ranging from 5 wt. % to 20 wt. %.

In some embodiments, the biological environmental interface 25 may be omitted from the structure depicted in FIG. 1. In some other embodiments, the interface structure 100 that is depicted in FIG. 1 may include two biological environmental interfaces 25, which would include a first biological environmental interface 25, as depicted in FIG. 1, and a second biological environmental interface (not depicted) on the opposing side of the composite electrical impulse generating layer 20 from the first biological environmental interface 25.

Still referring to the interface structure 100 that is depicted in FIG. 1, the composite electrical impulse generating layer 20 harvests mechanical energy in a form of minute omni-directional accelerations and decelerations, to transform this energy into electric impulses via piezo-electric effect in the crystals, i.e., nanocrystals 10, and the piezo-polymer 5. These impulses will be further distributed to the gold surface, i.e, the biological environmental interface 25, by the carbon nanotubes (CNTs) 15. Further, this composite electrical impulse generating layer 20 is expected to be sensitive to changes in the membrane depolarization of juxtapositioned neurons. The neuronal membrane depolarization is expected to transform into a mechanical stress of the layer. Thus, this composite material represents a bidirectional interface with an excitable tissue, e.g., a neuronal network in the brain and/or spinal cord. In some embodiments, the presence of CNTs 15 warrant electrons to go to the surface of the material, allowing a gradient for negative ions and negatively charged free radicals to enter the depth of the material via CNT, and distribute electrons within piezo-polymer and amongst piezo-crystals. For instance, free radical oxygen species, e.g. $H_2O_2$, $O_3^-$ etc) will enter the composite impulse generated layer 20 and transform into $H_2O$ and $CO_2$ (or $HCO_3^-$ (carbonate buffer).

It is noted that the form factor, number of type of material layers and material compositions for the material layers that are provided in FIG. 1 are only one example of an interface structure 100 that may be provided by the present disclosure.

Figure 2:
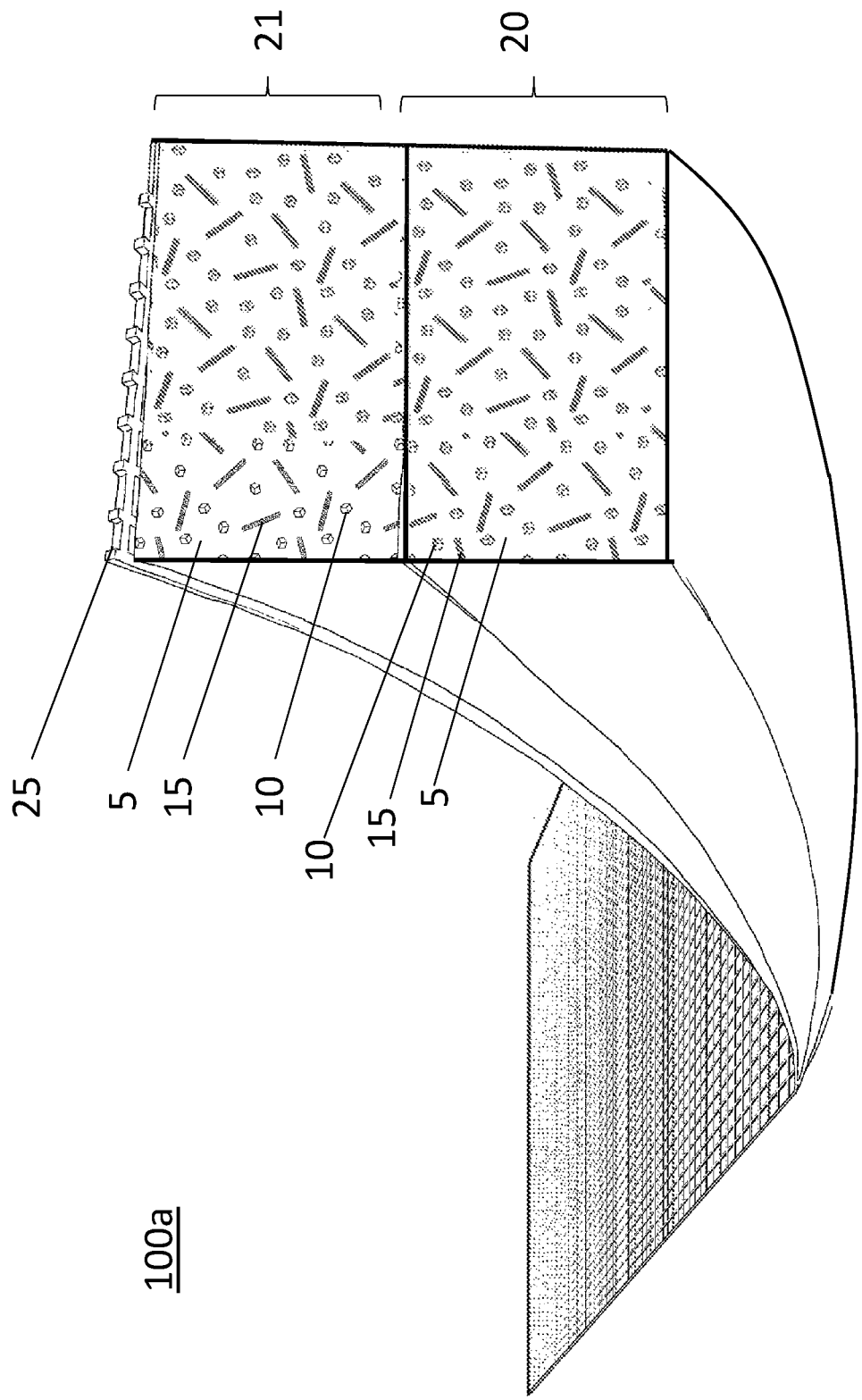
FIG. 2 is a perspective view of a neuron-computer bi-directional interface structure having a film and ribbon form factor, in which the interface structure is a multi-layered structure including a composite electrical impulse generating layer; a composite electrical impulse amplifying layer, and at least one biological environment interface layer having a grid geometry, in accordance with one embodiment of the present disclosure.

FIG. 2 depicts another embodiment of a neuron-computer bi-directional interface structure having a film and ribbon form factor, in which the interface structure 100a is a multi-layered structure including a composite electrical impulse generating layer 20; a composite electrical impulse amplifying layer 21, and at least one biological environment interface layer 25 having a grid geometry. Some aspects of the interface structure 100a depicted in FIG. 2 are similar to the interface structure 100 that is depicted in FIG. 1. For example, the description of the composite electrical impulse generating layer 20 and the biological environment interface layer 25 for the interface structure 100 that is depicted in FIG. 1 can provide a description for at least some examples of the composite impulse generating layer 20 and the biological environment interface layer 25 that is depicted in FIG. 2.

The composite electrical impulse amplifying layer 21 is present between the composite impulse generating layer 20 and the biological environment interface layer 25. The composite electrical impulse amplifying layer 21 is similar in its composition to the composite impulse generating layer 20. For example, similar to the composite impulse generating layer 20, the composite impulse amplifying layer 21 may include a matrix phase of a piezo polymer material 5, a first dispersed phase of piezo nanocrystals 10, and second dispersed phase of carbon nanotubes 15, in which the first and second dispersed phase presented through the matrix phase. However, the concentration of piezo nanocrystals 10 in the composite electrical impulse amplifying layer 21 is higher than the concentration of the piezo nanocrystals 10 in the composite electrical impulse generating layer 10. In one embodiment, the composite impulse amplifying layer 21 may include the piezo polymer 5 in an amount ranging from 10 wt. % to 30 wt. %; the piezo nanocrystals 10 may be present in an amount ranging from 70 wt. % to 89.9 wt. %; and carbon nanotubes (CNTs) in an amount ranging from 0.1 wt. % to 1.0 wt. %. In one example, the composite impulse amplifying layer 21 can include the piezo polymer material 5 in an amount equal to 24.5 wt. %, the nano crystals 10 in an amount equal to 70 wt. %, and the carbon nanotubes 15 may be present in an amount equal to 0.5 wt. %. For the purposes of comparison, the composite electrical impulse generating layer 20 may include the piezo polymeric material 5 in an amount ranging from 70 wt. % to 84.9 wt. %; piezo nanocrystals 10 in an amount ranging from 15 wt. % to 30 wt. %; and carbon nanotubes 15 in an amount ranging from 0.1 wt. % to 1 wt. %.

Further, the composite impulse amplifying layer 21 has a higher piezoelectric coefficient than the composite impulse generating layer 20. In some embodiments, the piezo-electric coefficient d33 of the composite impulse amplifying layer 21 can range from 50-500 pC/N; and the composite impulse amplifying layer 21 can have a polarization ranging from 3500-10000 mC/cm$^2$.

In some embodiments, the composite impulse amplifying layer 21 functions to receive electrical impulses from the composite impulse generating layer 20 and increases the magnitude/charge/of the electrical impulses. The composite impulse amplifying layer 21 also functions to transmit the electrical impulses to the biological environmental interface layer 25. It is noted that the composite impulse amplifying layer 21 also generates electrical impulses.

The thickness of the composite impulse amplifying layer 21 may range from 50 µm to 400 µm. In one example, the thickness of the composite impulse amplifying layer 21 is equal to 200 µm.

As noted above, with the exception of the difference in the concentration of the piezo nanocrystals 10, the composite impulse amplifying layer 21 and the composite impulse generating layer 20 are similar. Therefore, the examples in the descriptions of the piezo polymeric materials 5, the piezo nanocrystals 10, and the carbon nanotubes 15 provided above for the composite impulse generating layer 20 can provide examples for the piezo polymeric materials 5, the piezo nanocrystals 10, and the carbon nanotubes 15 that are present in the composite impulse amplifying layer 21. It is not necessary that the components, i.e., piezo polymeric material 4, piezo nanocrystals 10, and carbon nanotubes (CNTs), have the same compositions for both the composite impulse generating layer 20 and the composite impulse amplifying layer 21.

Still referring to FIG. 2, the composite electrical impulse generating layer 20 harvests mechanical energy in a form of minute omni-directional accelerations and decelerations, to transform this energy into electric impulses via piezo-electric effect in crystals and the piezo-polymer itself. These impulses will be further accepted by the composite electrical impulse amplifying layer 21, which will amplify these impulses due to the higher piezo-electric coefficient. These amplified impulses will be further distributed back to the gold surface, i.e., the biological environmental interface layer 25, via the carbon nanotubes (CNTs) 15.

This material is expected to be sensitive to changes in the membrane depolarization of juxtapositioned neurons. The neuronal membrane depolarization is expected to transform into a mechanical stress of the composite electrical impulse generating layer 20. This mechanical stress of the highly flexible composite electrical impulse generating layer 20 is transformed in the (with composite electrical impulse amplifying layer 21 (having a higher piezo-electric coefficient) into amplified electrical impulses. Thus, the composite material of the interface structure 100*a* depicted in FIG. 2 represents another embodiment of a bidirectional interface with an excitable tissue (neuronal network in the brain and/or spinal cord).

In some embodiments, the biological environmental interface 25 may be omitted from the structure depicted in FIG. 2. In some other embodiments, the interface structure 100 that is depicted in FIG. 1 may include two biological environmental interfaces 25, which would include a first biological environmental interface 25 in direct contact with the composite electrical impulse amplifying layer 21, as depicted in FIG. 2, and a second biological environmental interface (not depicted) on the opposing side of the interface structure 100*a*, e.g., on the exposed opposite face of the composite electrical impulse generating layer 20.

Figure 3:
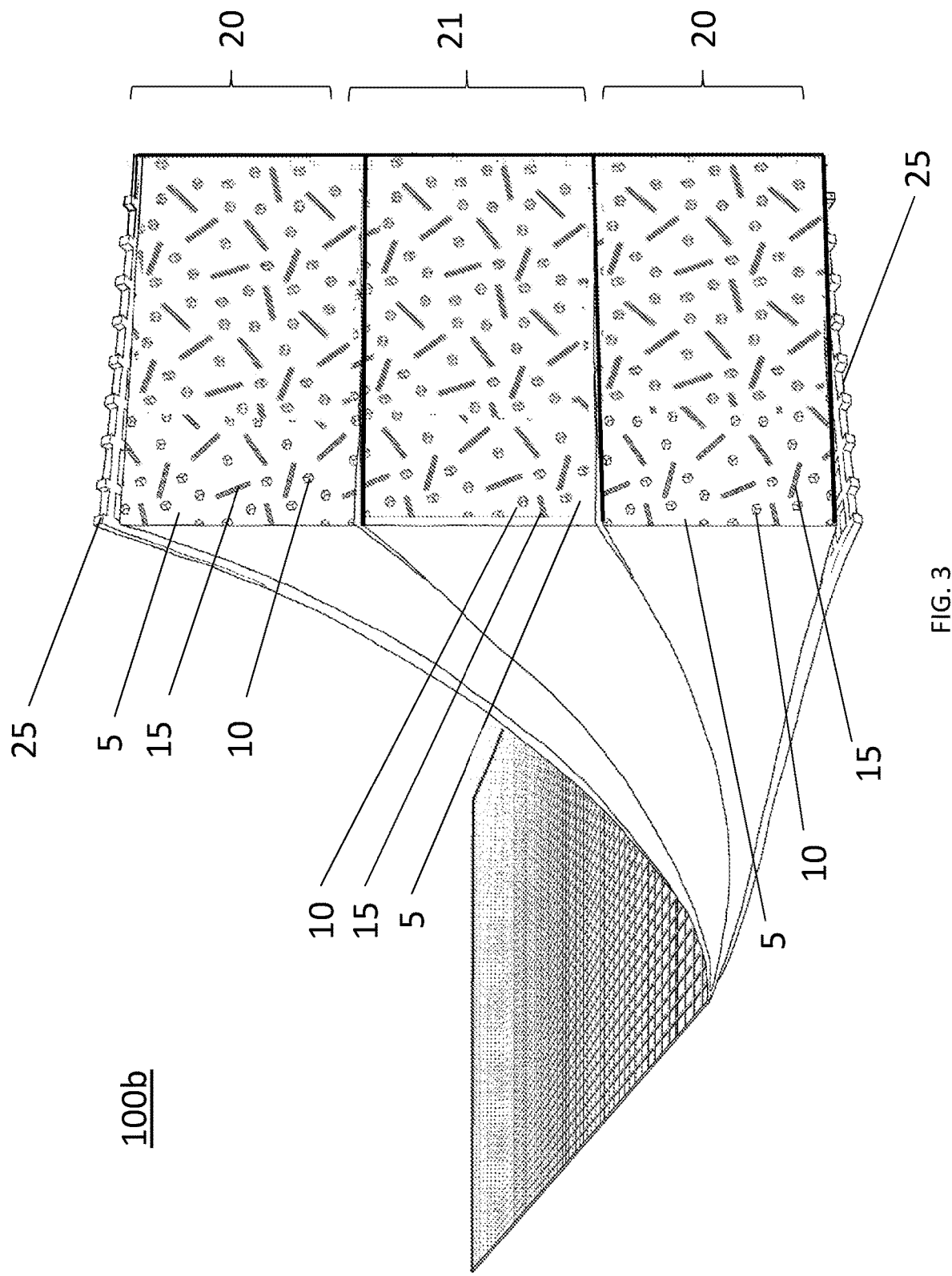
FIG. 3 is a perspective view of a neuron-computer bi-directional interface structure having a film and ribbon form factor, in which the interface structure is a multi-layered structure including a composite electrical impulse amplifying layer positioned between two composite electrical impulse generating layers; and at least one biological environmental interface layer having a grid geometry, in accordance with one embodiment of the present disclosure.

FIG. 3 depicts another embodiment of an interface structure 100*c*. In the embodiment that is depicted in FIG. 3, the interface structure 100*c* includes a composite electrical impulse amplifying layer 21 as the core of a interface structure 100*c* having a film/ribbon form factor, in which the composite electrical impulse amplifying layer 21 is present between two layers of composite electrical impulse generating layers 21. The composite electrical impulse generating layer 20 and the composite electrical impulse amplifying layer 21 that is depicted in FIG. 3 has been described above with reference to the embodiments depicted in FIGS. 1 and 2.

The interface structure 100*c* that is depicted in FIG. 3, includes a crystalline saturated layer provided by the composite electric impulse amplifying layer 21 that is situated between polymer saturated layers provided by the composite electric impulse generating layers 20 to provide a cascade amplifier of the direct piezoelectric effect. The cascade amplifier is produced by a stress-dependent change in polarization, which can be increased as result of the high flexibility and durability of the electric impulse generating materials, which also follow to improve a measurable potential difference across the material.

Referring to FIG. 3, in some embodiments, the bottom composite electrical impulse generating layer 20 (as orientated on in FIG. 3) is expected to harvest mechanical energy in a form of minute omni-directional accelerations and decelerations, to transform this energy into electric impulses via piezo-electric effect in the crystals and the piezo-polymer itself. The impulses are accepted by the centrally positioned composite electrical impulse amplifying layer 21, which amplifies these impulses due to the higher piezo-electric coefficient of the composite electrical impulse amplifying layer 21 when compared to the composite electrical impulse generating layer 20. Then electrical impulse from the centrally positioned composite electrical impulse amplifying layer 21 can then be applied to the top composite electrical impulse generating layer 20 (as orientated in FIG. 3). Following the application of electric charge the inverse/secondary piezoelectric effect, which is a deformation of the material, occurs. In the material that underwent poling such deformations lead to the compressive stress along the electro-magnetic field lines. This mechanical stress of the highly flexible layer top composite electrical impulse generating layer 20 is transformed in the composite electrical impulse amplifying layer 21 (with higher piezo-electric coefficient) into amplified electrical impulse. This effect is an example of a piezoelectric cascade amplifier and these amplified impulses will be further distributed back to the biological environmental interface 25 (which can be provided by a gold grid) via the carbon nanotubes 15.

The piezoelectric composite materials of the interface structure 100c depicted in FIG. 3 display coupled structural deformation in amplifier modes for such as in a shear or bend type structural deformation, where a shear deformation of the embedded piezoelectric material produces a largely bending deformation of the composite structure.

The composite material depicted in FIG. 3 represents a bidirectional interface with an excitable tissue, which can be suitable for interaction with a neuronal network in the brain and/or spinal cord.

In some embodiments, one or both of the biological environmental interfaces 25 may be omitted from the structure depicted in FIG. 3.

Figure 4:
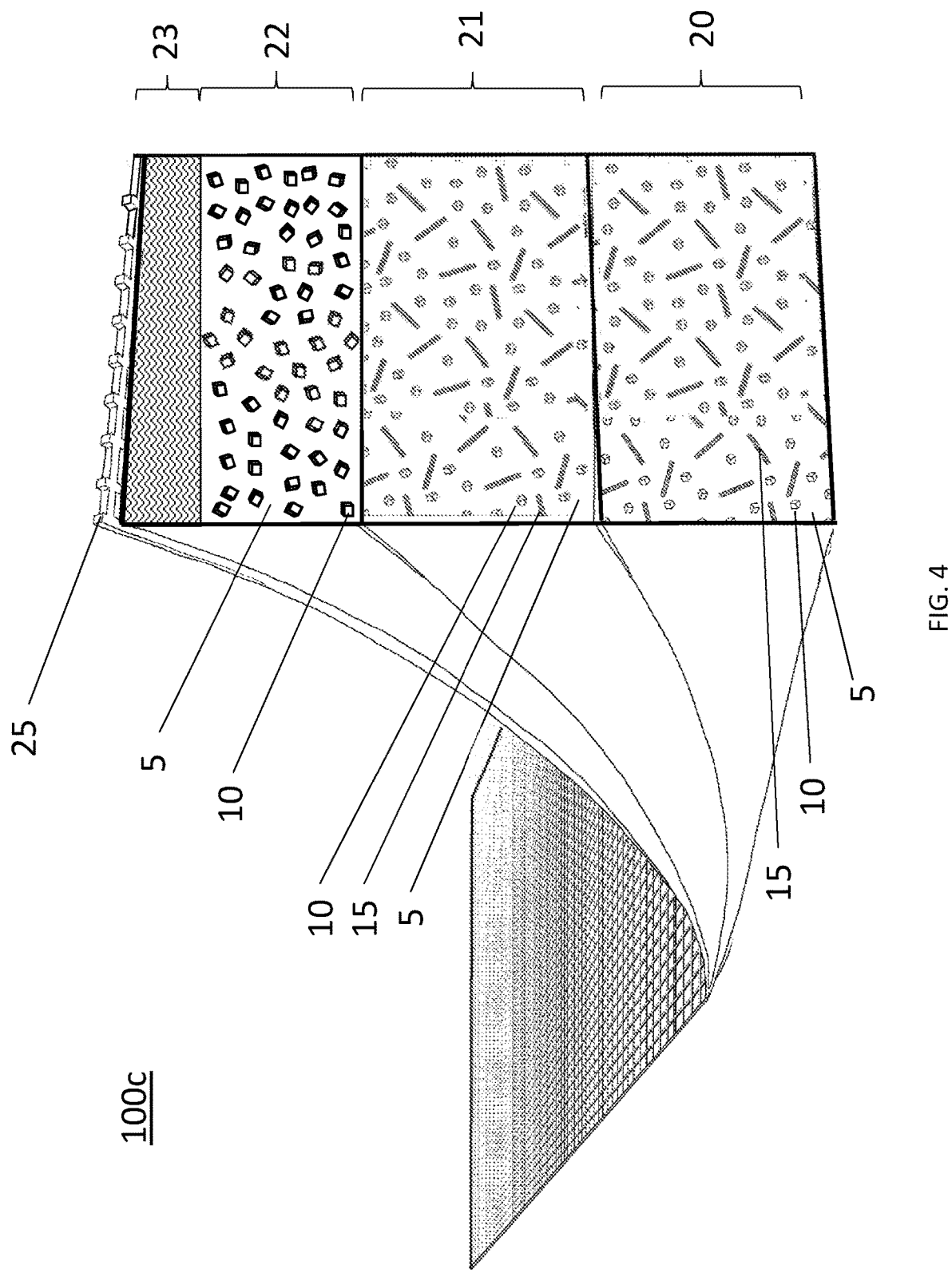
FIG. 4 is a perspective view of a neuron-computer bi-directional interface structure having a film and ribbon form factor, in which the interface structure is a multilayered stack including a composite electrical impulse generating layer, a composite electrical impulse amplifying layer, a piezoelectric composite layer free of carbon nanotubes, a resin layer and a biological environmental interface layer, in accordance with one embodiment of the present disclosure.

FIG. 4 illustrates another example of an interface structure 100c having a film and ribbon form factor, in which the interface structure 100c is a multilayered stack including a composite electrical impulse generating layer 20, a composite electrical impulse amplifying layer 21, a piezoelectric composite layer free of carbon nanotubes 22, a resin layer 23 and a biological environmental interface layer 25. The piezoelectric composite layer that is free of carbon nanotubes 22 and the resin layer 23 may be present as a bilayer positioned between the biological environmental interface layer 25 and the composite impulse amplifying layer 21 so that the resin layer 23 is in contact with the biological environmental interface layer 25 and the piezoelectric composite layer free of carbon nanotubes 22 is in contact with the composite impulse amplifying layer 21.

The composite electrical impulse generating layer 20 and the composite electrical impulse amplifying layer 21 have been described above with reference to FIGS. 1-3. The piezoelectric composite layer free of carbon nanotubes 22 includes a matrix of a piezo polymeric material 5 and a dispersed phase of a piezo nanocrystals 10. The piezo polymeric material 5 and the piezo nanocrystal material 10 that is employed in the piezoelectric composite layer that is free of carbon nanotubes 22 is similar to the piezo polymeric material 5 and piezo nanocrystal material 10 that is employed in the composite electrical impulse generating layer 20 and the composite electrical impulse amplifying layer 21.

In one embodiment, the piezoelectric composite layer that is free of carbon nanotubes 22 includes a piezo polymeric material 5 in an amount ranging from 10 wt. % to 30 wt. %, and the nanocrystals 10 are present in an amount ranging from 70 wt. % to 90 wt. %. In one example, the piezo electric composite layer that is free of carbon nanotubes 22 includes a piezo polymeric material 5 in an amount equal to 20 wt. %, and piezo nanocrystals in an amount equal to 80 wt. %. The thickness of the piezo composite layer that is free of carbon nanotubes 22 may range from 50 µm to 400 µm. In one example, the thickness of the piezo composite layer that is free of carbon nanotubes 22 may be equal to 200 microns.

In some embodiments, the piezo-electric coefficient d33 of the piezo composite layer that is free of carbon nanotubes 22 can range from 40-500 pC/N; and the piezo composite layer that is free of carbon nanotubes 22 can have a polarization ranging from 3100-10000 mC/cm$^2$.

The piezo composite layer that is free of carbon nanotubes 22 can be for generation and amplification of the signal due to the high piezo-crystal content of the layer. In some embodiments, the piezo composite layer that is free of carbon nanotubes 22 may function in a manner similar to the composite electrical impulse amplifying layer 21, but without the incorporation of carbon nanotubes.

The resin layer 23 may be composed of a polymer, such as sulfonated poly ether ether ketone (SPEEK) incorporated with micron-sized sulfonate styrene-crosslinked divinyl benzene-based cation exchange resin particles. The thickness of the resin layer 23 may range from 50 µm to 200 µm. In some examples, the resin layer 23 may provide for potassium-sodium (K—Na) ion exchange. The resin layer 23 is an ion-exchange material.

Figure 5:
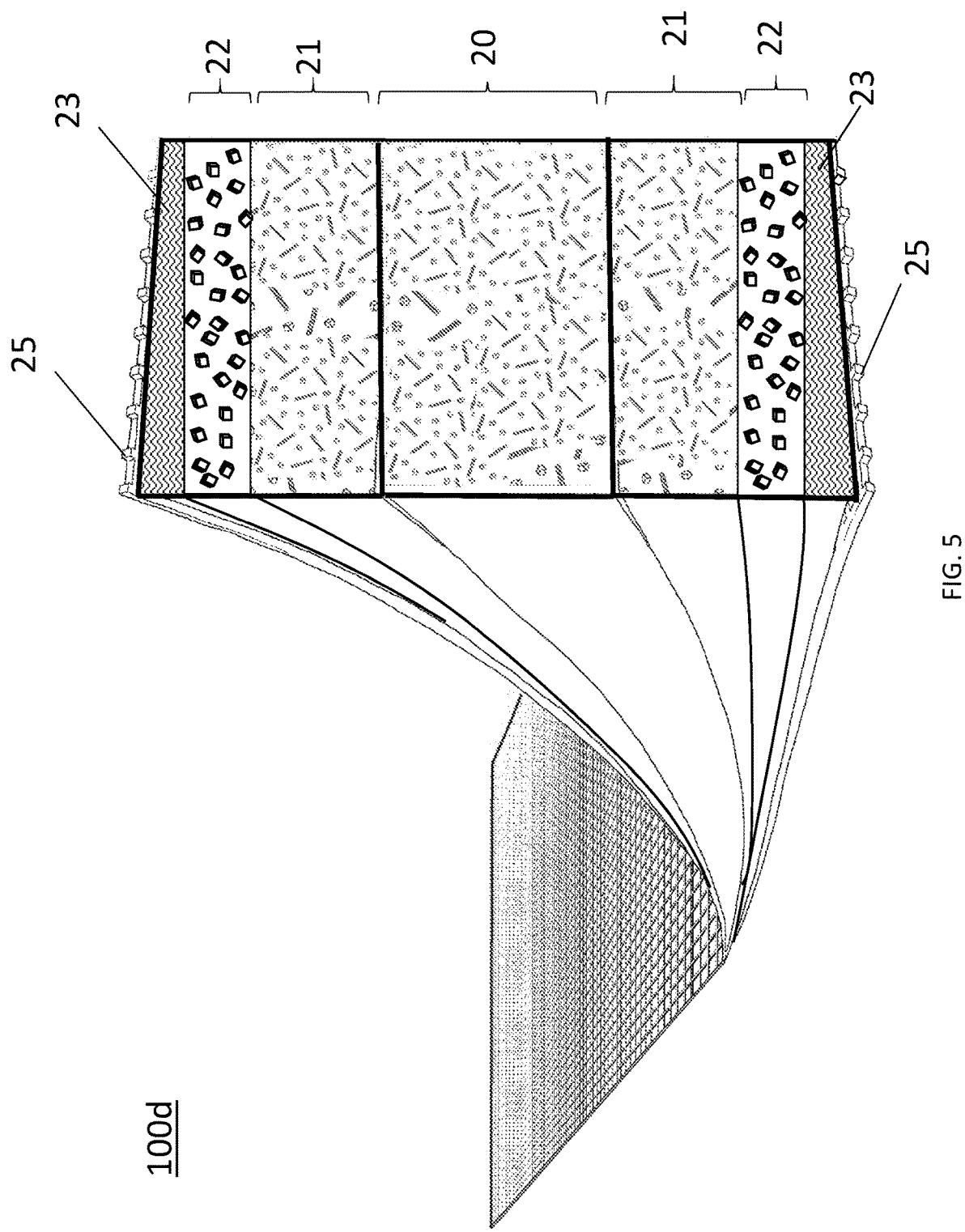
FIG. 5 is a perspective view of another embodiment of a neuron-computer bi-directional interface structure having a film and ribbon form factor, in which the interface structure is a multilayered stack including a first biological environmental interface layer, a first resin layer, a first piezoelectric composite layer free of carbon nanotubes, a first composite electrical impulse amplifying layer, a composite electrical impulse generating layer, a second composite electrical impulse amplifying layer, a second piezoelectric composite layer free of carbon nanotubes, a second resin layer and a second biological environmental interface layer.

It is noted that the bilayer of the piezo composite layer that is free of carbon nanotubes 22 and the resin layer 23 is not limited to only being incorporated into an interface structure as depicted in FIG. 4. For example, another embodiment of an interface structure is depicted in FIG. 5 having form factor in the geometry of a film/ribbon, and a multilayered stack including a first biological environmental interface layer 25 (at the bottom of the stack), a first resin layer 23, a first piezoelectric composite layer free of carbon nanotubes 22, a first composite electrical impulse amplifying layer 21, a composite electrical impulse generating layer 20, a second composite electrical impulse amplifying layer 21, a second piezoelectric composite layer free of carbon nanotubes 22, a second resin layer 23 and a second biological environmental interface layer 25. Each of these layers have been described above for structures having similar reference numbers. Further, one or both of the first and second biological environmental interface layer 25 may be omitted from the structures depicted in FIGS. 4 and 5.

Figure 6:
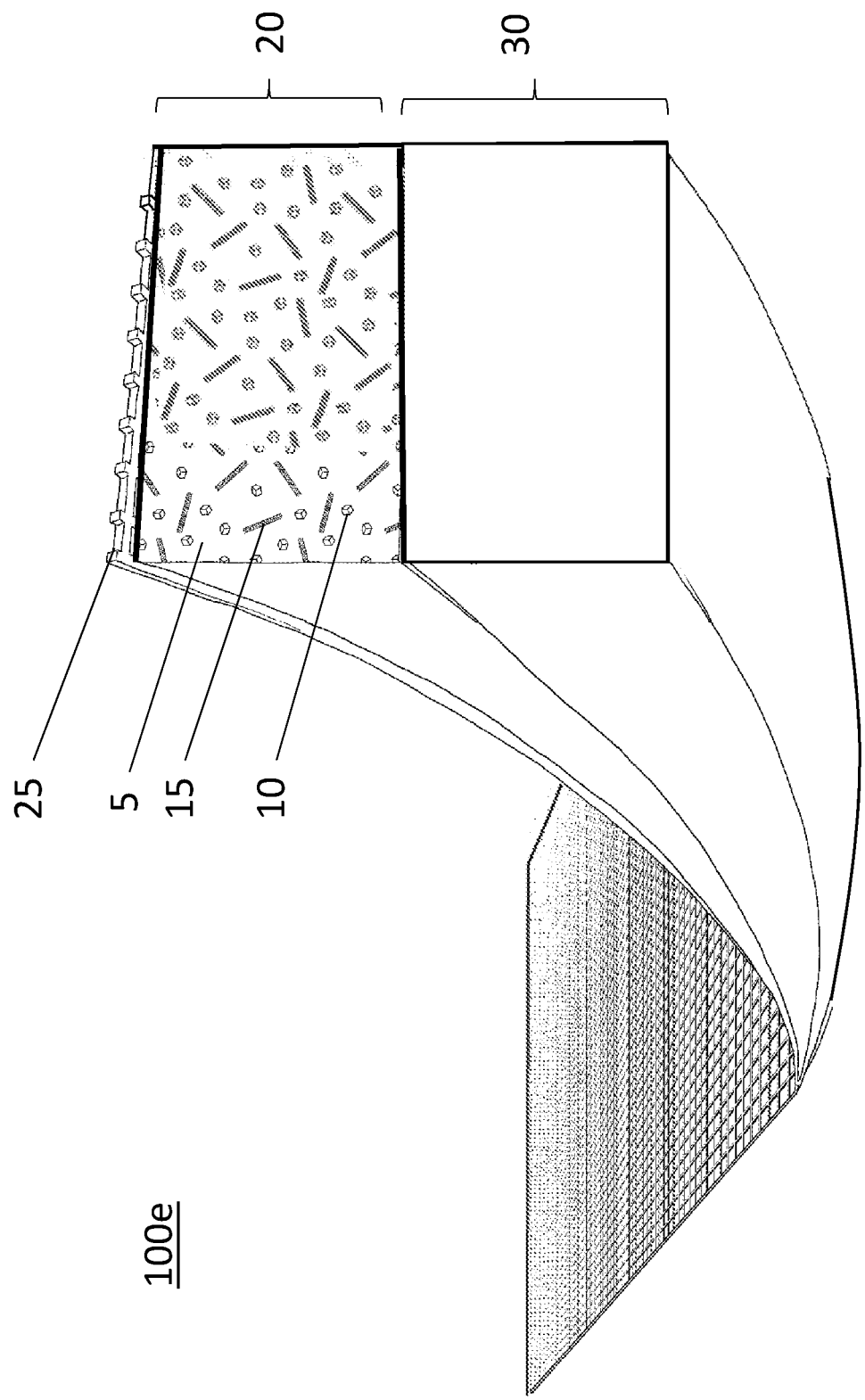
FIG. 6 is a perspective view of a neuron-computer bi-directional interface structure having a film and ribbon form factor, in which the interface structure is a multi-layered structure including a composite layer of a piezo polymeric matrix material, a first dispersed phase of piezo nanocrystal material, and a second dispersed phase of carbon nanotubes.

FIG. 6 depicts a neuron-computer bi-directional interface structure having a film and ribbon form factor, in which the interface structure is a multi-layered structure including a composite layer of a piezo polymeric matrix material 5, a first dispersed phase of piezo nanocrystal material 10, and a second dispersed phase of carbon nanotubes 15, a dielectric polymer layer 30, and at least one biological environment interface layer 25 having a grid geometry. The dielectric polymer layers employed in the interface structure 100e depicted in FIG. 6 may be composed of bio-compatible materials with high dielectric properties.

The dielectric polymer layer 30 can provide an isolating surface of the interface structure 100e that is depicted in FIG. 6. The dielectric polymer layer 30 may be composed of polydimethylsiloxane (PDMS). The PDMS empirical formula is $(C_2H_6OSi)_n$, and its fragmented formula is $CH_3[Si(CH_3)_2O]_nSi(CH_3)_3$, n being the number of monomers repetitions. Depending on the size of monomers chain, the non-cross-linked PDMS may be almost liquid (low n) or semi-solid (high n). The siloxane bonds result in a flexible polymer chain with a high level of viscoelasticity.

It is noted that PDMS is only one example of a dielectric polymer layer 30 that can be employed in an interface structure 100e for a neuron-computer bi-directional interface structure. For example, other dielectric polymer compositions may be provided by other mineral-organic polymer (a structure containing carbon and silicon) of the siloxane family. The dielectric polymer layer 30 may have a thickness ranging from 40 µm to 300 µm. In one example, the dielectric polymer layer 30 has a thickness of 100 µm.

The at least one biological environment interface layer 25 of the interface structure 100e depicted in FIG. 6 may be omitted.

FIG. 7 depicts another embodiment of an interface structure 100f including the dielectric polymer layer 30 that is described above with reference to FIG. 6. FIG. 7 depicts one embodiment of a neuron-computer bi-directional interface structure having a film and ribbon form factor, in which the interface structure 100f is a multi-layered structure including a dielectric polymer layer 30 positioned between two composite electrical impulse generating layers 20; and at least one biological environmental interface layer 25 having a grid geometry. More specifically, the interface structure 100f depicted in FIG. 7 includes to biological environmental interface layers 25 on opposing sides of the interface structure 100f. In some embodiments, one or both of the biological environmental interfaces 25 may be omitted from the structure depicted in FIG. 3.

In some embodiments, the aforementioned dielectric polymer composition, i.e., the dielectric composition for the dielectric polymer layer 30, can provide the matrix of a composite including piezo nanocrystals 10 and carbon nanotubes 15. The piezo nanocrystals 10 and carbon nanotubes 15 have been described above. The composite layer having the matrix of the dielectric polymer layer and dispersed phases of piezo electric materials, i.e., the piezo nanocrystals, and carbon nanotubes, the material layer may be referred to as a dielectric matrix composite with dispersed phases of piezo nanocrystals 10 and carbon nanotubes 15. In one example, the dielectric matrix composite with dispersed phases of piezo nanocrystals 10 and carbon nanotubes 15 includes the dielectric polymer, e.g., polydimethylsiloxane (PDMS), in an amount ranging from 70 wt. % to 84.9 wt. %, the piezo nanocrystals 10 in an amount ranging from 15 wt. % to 30 wt. % and the carbon nanotubes 0.1 wt. % to 1.0 wt. %. In one example, the dielectric matrix composite with dispersed phases of piezo nanocrystals 10 and carbon nanotubes 15 includes the dielectric polymer, e.g., polydimethylsiloxane (PDMS), present in an amount equal to 79.5 wt. %, the piezo nanocrystals 10 present is an amount equal to 20 wt. % and the carbon nanotubes 0.5 wt. %.

In one embodiment, the piezo-electric coefficient d33 of the dielectric matrix composite with dispersed phases of piezo nanocrystals 10 and carbon nanotubes 15 can range from 0.5-2 pC/N; and the piezo composite layer that is free of carbon nanotubes 22 can have a polarization ranging from 2500-3000 mC/cm$^2$.

In one example, the dielectric matrix composite with dispersed phases of piezo nanocrystals and carbon nanotubes may be incorporated into an interface structure having a film/ribbon form factor. For example, the dielectric matrix composite with dispersed phases of piezo nanocrystals and carbon nanotubes may be incorporated into an interface structure, as depicted in FIG. 6, in which the dielectric matrix composite with dispersed phases of piezo nanocrystals and carbon nanotubes is substituted for the dielectric polymer layer 30. In this embodiment, a composite electrical impulse generating layer 20 is present atop the dielectric matrix composite with dispersed phases of piezo nanocrystals and carbon nanotubes, and a biological environment interface layer 25 is present atop the composite electrical impulse generating layer 20. In this example, the dielectric matrix composite with dispersed phases of piezo nanocrystals and carbon nanotubes may have a thickness ranging from 40 μm to 300 μm. In one example, the dielectric matrix composite with dispersed phases of piezo nanocrystals and carbon nanotubes has a thickness of 100 μm.

In another example, the dielectric matrix composite with dispersed phases of piezo nanocrystals and carbon nanotubes may be incorporated into an interface structure, as depicted in FIG. 7, in which the dielectric matrix composite with dispersed phases of piezo nanocrystals and carbon nanotubes is substituted for the dielectric polymer layer 30 that is present between two composite electrical impulse generating layers 20.

FIGS. 1-7 illustrate only some examples of interface structures having a film/ribbon form factor. In other examples, an interface structure is provided that includes at least a bilayer of the piezo composite layer that is free of carbon nanotubes, and a layer provided by a mixture of piezo polymeric material and dielectric polymeric material.

The piezo composite layer that is free of carbon nanotubes for the bilayer is similar to the layer identified by reference number 22 in FIGS. 4 and 5).

For the layer provided by a mixture of piezo polymeric material and dielectric polymeric material, the piezo polymeric material may be similar in composition to the piezo polymer 5 of the composite electrical impulse generating layer 20. For example, the piezo polymer for the biological environmental interface layer 25 may be polyvinylidene fluoride trifluoroethylene (PVDF-TrFE). In some embodiments, the piezo polymer material may be mixed with a dielectric polymer, such as polydimethylsiloxane (PDMS). For example, the layer provided by the mixture of piezo polymer and dielectric polymer may include 70 wt. % to 90 wt. % piezo polymer, and 10 wt. % to 30 wt. % dielectric polymer. The layer provided by the mixture of the piezo polymer material may be characterized by a piezo-electric coefficient d33 ranging from 10-100 pC/N; and a polarization ranging from 1500-5000 mC/cm$^2$.

The interface structure including the bilayer of the piezo composite layer that is free of carbon nanotubes, and a layer provided by a mixture of piezo polymeric material and dielectric polymeric material may further include at least one biological interface layer (also referred to as outer layer) also composed of a polymeric material including a dispersed phase of carbon nanotubes. The carbon nanotubes may be present in an amount ranging from 5 wt. % to 20 wt. %.

In yet another example, the interface structure may include a stack of a layer provided by a mixture of piezo polymeric material and dielectric polymeric material that is positioned between two piezo composite layers that are free of carbon nanotubes.

The piezo composite layer that is free of carbon nanotubes is similar to the layer identified by reference number 22 in FIGS. 4 and 5.

The layer provided by the mixture of the piezo polymer material and dielectric material layer has been described above in the description of the bilayer of the piezo composite layer that is free of carbon nanotubes and the mixture of the piezo polymer material and dielectric material layer provides one example of the composition of the mixture of the piezo polymer material and dielectric material layer that is positioned between two piezo composite layers that are free of carbon nanotubes. In another embodiment, the mixture of the piezo polymer material and dielectric material layer includes 10 wt. % to 30 wt. % piezo polymer, and 70 wt. % to 90 wt. % dielectric polymer. The layer provided by this mixture may be characterized by a piezo-electric coefficient d33 ranging from 0.5-2 pC/N.

The interface structure including the stack of a layer provided by a mixture of piezo polymeric material and dielectric polymeric material that is positioned between two piezo composite layers that are free of carbon nanotubes may further include at least one biological interface layer (also referred to as outer layer) also composed of a polymeric material including a dispersed phase of carbon nanotubes. The carbon nanotubes may be present in an amount ranging from 5 wt. % to 20 wt. %.

It is noted that in one embodiment the film and ribbon form factor depicted in FIGS. 1-7, which is substantially a 2D geometry, may be manipulated to provide the geometry of a haphazard ribbon, as depicted in FIG. 8. In another embodiment, the film and ribbon form factor depicted in FIGS. 1-7, may be manipulated to provide the geometry of a mobious loop, as depicted in FIG. 9. In yet another embodiment, the film and ribbon form factor depicted in FIGS. 1-7, may be manipulated to provide the geometry of a coil, i.e., a rolled up matt, as depicted in FIG. 10.

The form factors depicted in FIGS. 1-10 may have exterior dimensions on a microscale, in which the greatest dimension, e.g., length of the form factor may range from 100-200 micrometers.

In another embodiment, an ultra-stretchable elastic-composite generator is provided by employing Ecoflex silicone rubber-based piezoelectric composites and long silver nanowire-based stretchable electrodes.

It is noted that the interface structures provided herein are not limited to the two dimensional film and ribbon form factors described with reference to FIGS. 1-7. In some embodiments, the form factor for the interface material 100g, 100h, 100I, 100k may be a three dimensional (3D) geometry, such as a sphere having columns/spikes extending from the surface of the sphere, a sphere without columns/spikes, a sponge, a dendritic structure, or a wire geometry structure, as depicted in FIGS. 11-16. The three dimensional form factors that are depicted in FIGS. 11-16 may have exterior dimensions in the mircoscale, e.g., having dimensions ranging from 100 µm to 200 µm. Further, some of the following form factors described with reference to FIGS. 11-16 maybe introduced to a living tissue in the form of an injectable suspension of said structures.

FIG. 11 is a neuron-computer bi-directional interface structure having a three dimensional form factor in the shape of a sphere having a plurality of spikes/columns extending from the outer surface of the sphere. The interface structure 100g depicted in FIG. 11 includes a nucleus 35 of a composite electrical impulse generating material that includes a piezo polymeric matrix with a first dispersed phase of a piezo nanocrystals and a second dispersed phase of carbon nanotubes. The material that provides the nucleus of the 35 is similar to the composite electrical impulse generating material 20 that is described above with reference to FIGS. 1-7 and the composite electrical impulse amplifying material 21 that is described above with reference to FIGS. 2-5. Therefore, the description of the compositions for the piezo polymer matrix 5, the piezo nanocrystals 10 and the carbon nanotubes 15 for the composite electrical impulse generating material 20 is suitable for the description of the piezo polymer matrix and the dispersed phases of the piezo nanocrystals and the carbon nanotubes for the nucleus of the sphere having the plurality of spikes/columns that is depicted in FIG. 11.

In some embodiments, the piezo polymer matrix is present in the nucleus 35 in an amount ranging from 10 wt. % to 30 wt. %, the piezo nanocrystals are present in the nucleus 35 in an amount ranging from 70 wt. % to 95 wt. %, and the carbon nanotubes are present in the nucleus 35 in an amount ranging from 5 wt. % to 30 wt. %. In one example, the nucleus 35 includes a piezo polymeric matrix in an amount equal to 20 wt. %, piezo nanocrystals in an amount equal to 70 wt. %, and the carbon nanotubes are present in an amount equal to 10 wt. %. The nucleus 35 may have a diameter ranging from 100 µm to 1000 µm. In one example, the nucleus 35 has a diameter that is equal to 500 µm.

The outer sphere 40 of the sphere structure depicted in FIG. 11 may be composed of composite material of a piezo polymeric material and piezo nanocrystals. The outer sphere 40 is composed of material that is similar to the piezoelectric composite layer free of carbon nanotubes 22 that is described above with reference to FIGS. 4 and 5.

Therefore, the description of the compositions for the piezo polymer matrix 5, and the piezo nanocrystals 10 for the piezoelectric composite layer free of carbon nanotubes 22 is suitable for the description of the piezo polymer matrix and the dispersed phases of the piezo nanocrystals for the outer sphere 40 of the sphere having the plurality of spikes/columns that is depicted in FIG. 11.

In some embodiments, the piezo polymer matrix is present in the outer surface 40 in an amount ranging from 70 wt. % to 90 wt. %, and the piezo nanocrystals are present in the outer surface 40 in an amount ranging from 10 wt. % to 30 wt. %. In one example, the outer sphere 40 includes a piezo polymeric matrix in an amount equal to 80 wt. %, and the piezo nanocrystals are present in an amount equal to 20 wt. %. The outer sphere 40 may have a thickness (measured from the surface of the core 35 to the outer surface of the outer sphere 40) ranging from 500 µm to 5000 µm. In one example, the outer sphere 40 has a thickness that is equal to 2000 µm.

Still referring to FIG. 11, the plurality of spikes/columns 45 extending from the outer surface of the sphere 40 may be composed of a majority of carbon nanotubes and piezo polymeric material. The carbon nanotubes and the piezo polymeric material employed in the spikes/columns 45 have been described above with reference to FIGS. 1-7. In one embodiment, the carbon nanotubes may be present in the spikes columns 45 in an amount ranging from 70 wt. % to 95 wt. %, and the piezo polymeric material may be present in an amount ranging from 5 wt. % to 30 wt. %.

The spikes/columns 45 have physical dimensions of a diameter on the order of 2 µm; an overall length on the order of 2000 µm (measured extending from the surface of the nucleus 35 to the tip of the spikes/columns 45 extending from the outer sphere 40), and a protrusion distance equal to 1 µm (measured from the surface of the outer sphere 40).

Still referring to FIG. 11, the outer surface of the sphere having a plurality of spikes/columns may have an electrically conductive layer present thereon, which can provide an biological environment interface layer. It is noted that any of the compositions described above for the biological environment interface layer 25 may provide this layer for the structure depicted in FIG. 11. For example, the outer surface of the sphere may include a gold layer having thickness ranging from 8 microns to 12 microns, and in one example being equal to 10 microns.

FIG. 12 depicts another embodiment of a neuron-computer bi-directional interface structure having a three dimensional form factor in the shape of a sphere having a nucleus 36 present within an outer sphere 41. In the embodiment that is depicted in FIG. 12 both the nucleus 36 and the outer sphere 41 are composed of composite materials including a piezo polymeric matrix, a first dispersed phase of piezo nanocrystals and a second dispersed phase of carbon nanotubes (CNTs). The nucleus 36 may be composed of composite composition that is similar to the composite electrical impulse amplifying layer 21 that is described above with reference to FIGS. 2-5. In some embodiments, the piezo polymer matrix is present in the nucleus 36 in an amount ranging from 10 wt. % to 30 wt. %, the piezo nanocrystals are present in the nucleus 36 in an amount ranging from 70 wt. % to 95 wt. %, and the carbon nanotubes are present in the nucleus 36 in an amount ranging from 5 wt. % to 20 wt. %. In one example, the nucleus 36 includes a piezo polymeric matrix in an amount equal to 20 wt. %, piezo nanocrystals in an amount equal to 70 wt. %, and the carbon nanotubes are present in an amount equal to 10 wt. %. The nucleus 36 may have a diameter ranging from 100 µm to 1000 µm. In one example, the nucleus 36 has a diameter that is equal to 500 µm.

The outer sphere 41 of the sphere structure depicted in FIG. 12 may be composed of composite material of a piezo polymeric material, piezo nanocrystals and carbon nanotubes. The outer sphere 41 is composed of material that is similar to the composite electrical impulse generating layer 20 that is described above with reference to FIGS. 1-7. In some embodiments, the piezo polymer matrix is present in the outer sphere 41 in an amount ranging from 70 wt. % to 95 wt. %, the piezo nanocrystals are present in the outer sphere 41 in an amount ranging from 15 wt. % to 30 wt. %, and the carbon nanotubes are present in an amount ranging from 5 wt. % to 20 wt. %. In one example, the outer sphere 41 includes a piezo polymeric matrix in an amount equal to 70 wt. %, the piezo nanocrystals are present in an amount equal to 20 wt. %, and the carbon nanotubes are present in an amount equal to 10 wt. %. The outer sphere 41 may have a thickness (measured from the surface of the core 35 to the outer surface of the outer sphere 41) ranging from 500 µm to 5000 µm. In one example, the outer sphere 41 has a thickness that is equal to 2000 µm.

Still referring to FIG. 12, the outer surface of the sphere may have an electrically conductive layer present thereon, which can provide an biological environment interface layer. It is noted that any of the compositions described above for the biological environment interface layer 25 may provide this layer for the structure depicted in FIG. 12. For example, the outer surface of the sphere may include a gold layer having thickness ranging from 8 microns to 12 microns, and in one example being equal to 10 microns.

FIG. 13 depicts a neuron-computer bi-directional interface structure having a three dimensional form factor in the shape of a sponge (identified as interface structure 100i). FIG. 14 depicts a neuron-computer bi-directional interface structure having a three dimensional form factor in the three dimensional blot (identified as interface structure 100g). In some instances, the three dimensional blot interface structure 100g may be referred to as a dendritic geometry. The dendritic geometry can results from the application of an injectable "electrode" in the form of a suspension that polymerizes in the neuron-glial meshwork in situ. In this example, the nano-particles of the piezo-material are to be suspended in the liquid biocompatible polymer composition that promptly polymerizes in the targeted area in the "dendrite-like" distributed fashion. Such "distributed dendrite-like" electrode will provide an intimate functional bi-directional interface with the cellular membranes. The currently available metal point electrodes are lacking these features.

In one embodiment, the material that provides the sponge and three dimensional blot interface structures 100i, 100g may be a composite of piezoelectric materials and carbon nanotubes. In one example, the composite material that provides the sponge and three dimensional blot interface structures 100i, 100g can include a piezo polymeric material in an amount ranging from 70 wt. % to 95 wt., piezo nanocrystals in an amount ranging from 15 wt. % to 30 wt. % and carbon nanotubes present in an amount ranging from 0.1 wt. % to 1 wt. %. The composite material employed in the interface structures 100i, 100g is similar to the composite electrical impulse generating layer 20 and the composite electrical impulse amplifying layer 21. Therefore, the description of the compositions for the piezo polymer matrix 5, the piezo nanocrystals 10 and the carbon nanotubes 15 for the composite electrical impulse generating layer 20 and the composite electrical impulse amplifying layer 21 is suitable for providing at least one example for these materials applied to the interface structures 100i, 100j depicted in FIGS. 13 and 14. For example, the piezo polymeric material 5 may be polyvinylidene fluoride trifluoroethylene (PVDF-TrFE).

In another embodiment, the composition of a piezo polymeric material such as polyvinylidene fluoride trifluoroethylene (PVDF-TrFE) for the interface structures 100i, 100j depicted in FIGS. 13 and 14 may be substituted with a polymeric material selected for enhanced biocompatibility, such as polyanhydride poly-[bis(p-carboxyphenoxy)propane-sebacic acid] copolymer (PCPP-SA). In some embodiments, the sponge and three dimensional blot interface structures 100i, 100g may be porous structures having a pore diameter ranging from 5 µm to 20 µm.

The three dimensional blot interface structure 100g having dendritic geometry may be injected into tissue and formed therein from a liquid polymer with suspended piezoelectric nano-crystals. Once injected in tissue (approximate volume 3-5 cubic mm) the material promptly polymerizes, so the suspended nano-crystals become embedded in (semi-)rigid polymer matrix. The embedded nano-generators will be positioned in the immediate proximity of the membranes of the excitable elements of the brain, i.e. neurons (soma, axons, and dendrites) as well as of glial cells. We anticipate that these excitable cells will amplify and propagate impulses according to their physiologic projections.

FIGS. 15 and 16 depict some embodiments of a neuron-computer bi-directional interface structure having a three dimensional form factor having a wire type geometry. The wire type geometry may include an inner core 50 and an outer layer 55 that are each comprised of electrical impulse generating composites including a piezo polymeric material, piezo nanocrystals and carbon nanotubes. The inner core 50 may have a higher concentration of piezo nanocrystals than the outer layer 55. For example, the inner core 50 may be composed of 70 wt. % to 95 wt. % piezo nanocrystals and the outer layer 55 may be composed 15 wt. % to 30 wt. % piezo nanocrystals. The inner core 50 may also be composed of 10 wt. % to 30 wt. % piezo polymeric material, and 5 wt. % to 20 wt. % carbon nanotubes. The outer layer 55 may also be composed of 70 wt. % to 95 wt. % piezo polymeric material, and 5 wt. % to 20 wt. % carbon nanotubes. The inner core 50 may have a radius ranging from 10 µm to 80 µm, while the outer layer 55 may have a thickness ranging from 4 to 30 The exterior surface of the wire may include a dielectric polymer layer. The dielectric polymer can be polydimethylsiloxane (PDMS). FIG. 16 depicts a plurality of wires, which may each have a multilayered structure having compositions described with reference to FIG. 15.

In another embodiment, the neuron-computer bi-directional interface structure may be provided by a paste geometry that enables application of the material into voids, which can be across non-linear pathways. The paste may be applied in a three layered paste that includes an inner layer a middle layer and an outer layer. The inner layer may be referred to as a core paste material and may include a composite material of piezo polymeric material, piezo nanocrystals, and carbon nanotubes. In one example, the piezo polymer may be present in the core layer in an amount ranging from 10 wt. % to 30 wt. %, the piezo nanocrystals may be present in the core layer in an amount ranging from 70 wt. % to 89.9 wt. %, and the carbon nanotubes may be present in an amount ranging from 0.1 wt. % to 1 wt. %. In one example, the piezo polymer may be present in the middle layer in an amount ranging from 70 wt. % to 84.9 wt. %, the piezo nanocrystals may be present in the core layer in an amount ranging from 15 wt. % to 30 wt. %, and the carbon nanotubes may be present in an amount ranging from 5 wt. % to 20 wt. %. The piezo polymer material for the paste is similar to the piezo polymer material 5 that is described above with reference to FIG. 1. Similarly, the piezo nanocrystals and the carbon nanotubes for the paste are similar to the piezo nanocrystals 10 and the carbon nanotubes 15 that are described above with reference to FIG. 1.

The outer layer of the paste may be include a mixture of a dielectric polymer and a piezo polymer. For example, the piezo polymer for the outer layer may be polyvinylidene fluoride trifluoroethylene (PVDF-TrFE). In some embodiments, the dielectric polymer for the outer layer may be polydimethylsiloxane (PDMS). In some embodiment, the mixture of the dielectric polymer and the piezo polymer may include piezo polymer in an amount ranging from 20 wt. % to 60 wt. %, and dielectric polymer in an amount ranging from 70 wt. % to 90 wt. %. In some embodiments, the mixture of the dielectric polymer and the piezo polymer may include metal nanoparticles in an amount ranging from 30 wt. % to 60 wt. %. The metal nanoparticles may composed of any metal, such as gold (Au), platinum (Pt), iridium (Ir) or combinations thereof. In some embodiments, the mixture of the dielectric polymer and the piezo polymer may include carbon nanotubes in an amount ranging from 5 wt. % to 20 wt. %. In yet another embodiment, the outer layer may include a plurality of pores to provide a porous structure.

The piezo polymer material is similar to the piezo polymer material 5 that is described above with reference to FIG. 1.

In some embodiments, at least some elements of some of the interface structures described with reference to FIGS. 1-16 can be manufactured using pixilation and target doping, 3D printing, digital projection printing, lamination, hot press technology, and combinations thereof. The piezo polymeric material that provides the matrix for a number of the aforementioned polymers may be produced by spin casting from slurry; spray-pyrolysis; directed polymerization; molecular layer epitaxy (MLE) methods, self-assembled solid-state mixtures, and combinations thereof.

The structures depicted in FIGS. 1-16 are piezo-electric material structures, each with dimensions from nano-to-micro scale, which generate electrical impulses during any movement due to displacements of the piezo-electric material in respect to polymer matrix and/or bending of the piezo-electric crystals. The electric impulses are generated from the movement of said polymer-piezo-electric element system. All nano-to-micro electrodes operate in parallel, so the resulting power is accumulating from each electrode.

Being implanted in biological system, the electric charges are to be generated during the movement: walking, physical activity, head nodding and other like movements. The interface structures described herein can provide for neuronal stimulation at energies lower than in the currently available. Such lower output "power" is estimated to be sufficient to facilitate the cellular physiological functions in excitable cells (e.g. neurons). For example, the density of piezo-electric material in the polymer can be about $10^2$-$10^4$ piezo-electric elements per 1 $mm^2$ of the polymer matrix. In other examples, it is estimated that the composite material described with reference to FIGS. 1-16 when having dimensions of 250×200×3 mm will produce a converted output voltage and current signals at about ~10 V and 1.3 µA, respectively, showing stability and durability without degeneration under the repeated bending cycles.

In some embodiments, the proposed technology, as described in the interface structures 100, 100a, 100b, 100c, 100d, 100e, 100f, 100g, 100h, 100i, 100j, 100k, 100l, as depicted in FIGS. 1-16, operate in pseudo-continuous regime, in which the electrical impulses are generated each time the position of the piezo-structures (or their parts) changes in space. This is in dissimilarity with the impulse operation mode of the contemporary neuro-stimulatory technologies and devices.

In some of the above described embodiments, in order to amplify the electric charge generation (if needed), an thin (nano-scale) crystal layer with piezo-electric properties is placed on the outer surface of the polymer device. The nano-porous thin layer of piezo-polymer will be placed as an inner layer of the 2D structure (or in the center of the 3D structure). This polymer layer contains carbon nano-tubes in order to facilitate a small molecule (water and ions) exchange between the piezo-electric composite material and a neuron, and the extracellular space. The increase of the CNT concentration in polymer mixture leads to the increase of the electrical conductivity, thus negating the piezo-electric properties. In some embodiments, the nano-porous thin layer of piezo-polymer of carbon nano-tubes may be deposited as an inner layer for adsorption in order to facilitate the ion exchange with piezo-electric composite material, and for the removal of the free radicals (e.g. $O_3^-$ from the extracellular environment).

In some embodiment, the nano-polymer matrix, e.g., composite material that provides the sponge identified as interface structure 100i in FIG. 13, and the three dimensional blot identified as interface structure 100g in FIG. 14, may have nano-porous material layer, providing an ion exchange between piezo material and extracellular compartment. This property will facilitate the removal of the $O_3^-$ ions and other aggressive Oxygen derived free radicals from the vicinity of the electrode and from the extracellular compartment.

This nano-porous thin layer of neutral polymer or carbon nano-tubes may be deposited as an outer layer for adsorption in order to facilitate the ion exchange with piezo-electric composite material, and the removal of the free radicals (e.g. $O_3^-$) from the extracellular compartment. This layer is composed of nano-porous Graphene enriched with Fe/Co—N active sites.

The interface structures 100, 100a, 100b, 100c, 100d, 100e, 100f, 100g, 100h, 100i, 100j, 100k, 100l that are depicted in FIGS. 1-16 can provide biocompatible sustainable self-powered bi-directional neuron-silica interface technology that can be integrated in the neuron-glial network.

The proposed interface structures 100, 100a, 100b, 100c, 100d, 100e, 100f, 100g, 100h, 100i, 100j, 100k, 100l that are depicted in FIGS. 1-16 generate electric impulses via piezo-electric effect in nano-crystals through mechanical movement. The applications of these charges are vast-electro-stimulation of any excitable tissue (e.g. neurons, Deep Brain Stimulation for Parkinson's disease.

The proposed structures are bi-directional functional neuron-silica interfaces, in which manipulating the surface charges generated by the device based on the piezoelectric effects described above can provide for communication to a natural neuron or neuronal network. At the same time, the bi-directional functional neuron-silica interfaces is able to "read" the changes on the surface of the natural neuron. The potential applications of such technology are vast, e.g., all types and kinds of neuro-prosthetics and brain-computer interface with machine learning, feedback, etc.

The neuron-computer bi-directional interface structures, i.e., interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16, can be used for brain-computer interface and local electro-stimulation. In some embodiments, the neuron-computer bi-directional interface structures generate the electricity locally, with no wires, and no external battery. Further, the neuron-computer bi-directional interface structure are biocompatible, i.e., not just a neutral material, but a composite material, which will be accepted by neurons as a familiar environment due to it's naturalistic surface properties. It will be able to generate electrical impulses inside itself and accumulate charges on its surface. These charges will be of the same scale as "natural" charges on the surface of a natural neuron.

In some embodiments, because of the biocompatibility it is anticipated that the interface structures described herein will work in much lower voltages than conventional devices. For example, the interface structures might be a "circle"—low voltage, which equates to better biocompatibility, which in turn, makes the tissue more susceptible for lower voltages. In some embodiments, to make biocompatibility even better we have a "feature" of accepting free radicals ($H_2O_2$ and other species), degrade it to $H_2O$ and $HCO_3-$ (or $CO_2$) and an electron (which will be used for re-charging piezo-elements). This anti-oxidant effect is also adding to enhanced biocompatibility.

In the context of neurodegenerative disease, where neurons are progressively dying and the neuronal network is therefore disrupted, the interface structures provided herein can offer the surviving neurons a substrate that looks like neurons and feels like neurons. Similarly, in cases where the neuronal network is disrupted by other mechanism such as trauma, inflammation/demyelination, or malformation. The surviving neurons will react to our artificial neuron in a "friendly and accepting" manner, and charges that are generated in an "artificial neuron" via piezo-electric effect will be picked up by surviving neurons and facilitate/augment their function. This will help to restore the neuronal network, which was the damaged by the disease or trauma.

In one example, the above described neuron-computer bi-directional interface structures will be able to remove free radicals (oxygen species, e.g. O3− ions) from extracellular compartment, thus decreasing the oxidative stress and lipids' peroxidation, including cellular membranes and myelin.

The interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 are creating an interface between an electrode and a neuron (or neuronal network). This interface will be bi-directional. Manipulating the charges generated by the artificial neuron provides for communication with the natural neuron or neuronal network. At the same time, the interface structures can read the changes on the surface of the natural neuron.

The interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 may be devices can be autonomous (no wires to the computer) or wired to the computer. The autonomous devices can: (i) harvest mechanical energy; (ii) transform in to the electrical impulses; (iii) deliver impulses to neuronal network locally. The activity of the autonomous devices can be regulated via external magnetic field. This mechanism is related to the "poling". The interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 devices can also be non-autonomous devices. Non-autonomous devices can be regulated via wires as any other wired devices. For a non-autonomous device, the interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 may be employed as the leads/electrodes.

In some embodiments, the surface of the interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 act as a low-voltage sensor: the signal from a neuron is "sensed" by the outer layer, transferred to the deeper layers, and amplified in the layers with high concentration of crystals, and transferred via wires to the computing device, e.g., machine learning, prosthetics, robotics, etc.

The interface structures are designed to be low voltage biocompatible surface, in which the charges/impulses are adjusted to the range neurons generate naturally (action potential range).

In some embodiments, the in situ electro-stimulation that can be provided by the interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 will not only augment the neuronal network function, but also facilitate neuronal neurogenesis and the increase of the dendritic density. Overall advantages can include facilitation and maintenance of existing neuronal network, re-wiring via axonal sprouting and the increase of the dendritic density, neurogenesis stimulation/facilitation and a new neuronal network formation.

In some embodiments, the impulses generated by the nano-structures included in the interface structures 100, 100*a*, 100*b*, 100*c*, 100*d*, 100*e*, 100*f*, 100*g*, 100*h*, 100*i*, 100*j*, 100*k*, 100*l* that are depicted in FIGS. 1-16 can be modified and/or amplified with a powerful magnetic field, both constant (static) and/or variable, thus providing an external control over the device.

For example, the piezo-electric composite polymer-crystal material has ferromagnetic properties. In order to compensate the possible polarization in the high-energy magnetic field (e.g. MRI machines) and to make our material magnetically neutral, spintronics technology (spin transport electronics) can be employed. The spintronics technology comprises two ferromagnetic layers separated with the carbon nano-tube dielectric layer. In one option, i.e., option one, the ferromagnetic layers will undergo polarization without any external magnetic field before the assembly of the composite material. While in the Constant (Static) or Variable magnetic field only a very small fraction of spins will get synchronized, thus the resulting direction of the impulses will overall remain random.

In a second option, the ferromagnetic layers can be polarized in the same magnetic field. In such option of the composite material, the resulting impulses will be amplified being further exposed to the external magnetic field. The direction of generated piezo-electric impulses can be manipulated by the tuning of the external magnetic field. The direction of impulses can by synchronized, allowing the diode-like effect. This technology provides for a desired number of impulses to the desired direction in optimizable patterns.

In a third option, the ferromagnetic layers undergo polarization in the magnetic fields of opposite directions separately, before the assembly into the composite material; and, therefore, being assembled with a dielectric layer in between, will compensate the external magnetic field. Giant Magnetoresistance (GMR) is then applied to the structure. This option provides that the composite material is magnetically neutral in the external high-energy magnetic fields (e.g. MRI machines). The generated piezo-electric impulses are 3 distributed at random without the external magnetic field. The external Constant (Static) magnetic field will lock the impulses. The Variable magnetic field will synchronize the spins accordingly, but the direction of the impulses will remain random. Two variants of GMR that can be employed with the composite structures described above with reference to FIGS. 1-16 include: (1) current-in-plane (CIP), where the electric current flows parallel to the layers and (2) current-perpendicular-to-plane (CPP), where the electric current flows in a direction perpendicular to the layers. Options two and three of the above described spintronics technology can provide a composite material can be also viewed as a sensitive magnetic field sensor.

Although the invention has been described generally above, the following examples are provided to further illustrate the present invention and demonstrate some advantages that arise therefrom. It is not intended that the invention be limited to the specific examples disclosed.

EXAMPLES

Four example compositions were formed for testing. Composite 1 was a piezoelectric composite that was composed of 20% piezoelectric crystals ($Pb(Mg_{1/3}Nb_{2/3})O_3$—$PbTiO_3$ (PMN-PT)); 79% piezoelectric polymer PVDF-TrFE and 1% carbon nanotubes (CNTs). Composite 2 was a piezoelectric composite including 70% piezoelectric crystal ($Pb(Mg_{1/3}Nb_{2/3})O_3$—$PbTiO_3$ (PMN-PT)); 29% piezoelectric polymer PVDF-TrFE and 1% CNT. Composite 3 was a three layered structure including a core layer having the composition of composite 2 and outer layers having the composition of composite 1. Composite 4 was a three layered structure including a core layer having the composition of composite 1 and outer layers having the composition of composite 2. For composite 4, the core layer was sprayed with 0.5 ml of Dimethylformamide to improve adhesion between layers.

All composites underwent poling under the following conditions: Temperature: 50° C., Voltage: 4000-10 000V and Time: 3-10 minutes.

The piezoelectric charge coefficient was measured for composites 1, 2, and 3; and the piezoelectric voltage coefficient was measured for composites 1 and 2 The piezoelectric charge coefficient d33 for composite 1 was equal to 30 pC/N; and the piezoelectric charge coefficient d33 for composite 2 was equal to 31 pC/N; and the piezoelectric charge coefficient d33 for composite 3 was 30 pC/N. The piezoelectric voltage coefficient $g_{33}$ for composite 1 was equal to 14.3 mV*m/N; and the piezoelectric voltage coefficient g33 for composite 2 was equal to 16.5 mV*m/N.

Further, the composite multilayered materials showed increased piezoelectric coefficients. For example, the piezoelectric charge coefficient d33 increases from measures ~280 pC/N in Composite 1 compared to ~320 pC/N in Composite 3. The piezoelectric voltage coefficient g33 increased from measures ~14 mV*m/N in Composite 1 compared to ~17 mV*m/N in Composite 3.

The composite materials showed the following piezoelectric effect (CH1) parameters in mono-layered compared to multi-layered configurations:

10 Hz oscillations: Composite 1=156 mV
10 Hz oscillations: Composite 3=240 mV

Having described preferred embodiments of a self-powered bi-directional neuron-electronic device interface technology (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. An interface structure for a biological environment comprising:
at least one composite electrical impulse generating layer having a matrix phase of a piezo polymer material, a first dispersed phase of piezo nanocrystals, and second dispersed phase of carbon nanotubes, the first dispersed phase and second dispersed phase presented through the matrix phase,
wherein the piezo polymer material and first dispersed phased of piezo nanocrystals convert mechanical motion into electrical impulses and accept electrons to charge the at least one composite impulse electrical generating layer, and the second dispersed phase of carbon nanotubes provide pathways for distribution of the electrical impulses to a surface of the at least one composite impulse electrical generating layer contacting the biological environment, and delivery of byproducts of free radical degradation from the biological environment to both the first dispersed phase of piezo nanocrystals and the piezo polymer material, wherein the piezo polymer material is polyvinylidene fluoride trifluoroethylene having a beta (β) phase.

2. The interface structure of claim 1, further comprising at least one biological environment interface layer in contact with the surface of the at least one composite electrical impulse generating layer to provide a multi-layered interface structure, the electrical impulses reaching the surface of the at least one composite electrical impulse generating layer transmitted by at least one biological environmental interface layer to stimulate cells in the biological environment.

3. The interface structure of claim 1, wherein the interface structure has a two-dimensional form factor having a geometry of a ribbon, a sheet or a combination thereof.

4. The interface structure of claim 3, further comprising at least one composite electrical impulse amplifying layer having an amplifying matrix phase of the piezo polymer material, the first dispersed phase of the piezo nanocrystals, and the second dispersed phase of the carbon nanotubes, the first dispersed phase and the second dispersed phase presented through the amplifying matrix phase, wherein the at least one composite electrical impulse amplifying layer has a higher piezoelectric coefficient than the at least one composite electrical impulse generating layer, the at least one composite electrical impulse amplifying layer receiving electrical impulses from one at least one composite electrical impulse generating layer and increasing a magnitude of charge of electrical impulses, and transmitting to the at least one biological environmental interface layer.

5. The interface structure of claim 4, wherein the composite electrical impulse amplifying layer includes said piezo polymer material present in a wt. % ranging from 10% to 30%, the piezo nanocrystals present in a wt. % ranging from 70% to 89.0%, and the carbon nanotubes present in a wt. % ranging from 0.1 to 1.

6. The interface structure of claim 5, wherein the at least one composite electrical impulse generating layer comprises two composite impulse generating layers, wherein one of said two composite impulse generating layers is present on opposing sides of the composite electrical impulse amplifying layer to provide a cascade amplification of a piezoelectric effect resulting from stress-dependent change in polarization.

7. The interface structure of claim 6, wherein the at least one biological environmental interface layer comprises two grid structures on opposing sides of a material stack that provides the interface structure including the at least one composite electrical impulse generating layers and the at least one composite electrical impulse amplifying layers.

8. The interface structure of claim 5, further comprising a bilayer of a resin layer and a piezoelectric composite layer free of carbon nanotubes, wherein the bilayer is positioned between the biological environmental interface layer and the composite electrical impulse amplifying layer so that the resin layer is in contact with the biological environmental interface layer and the piezoelectric composite layer free of carbon nanotubes is in contact with the composite impulse amplifying layer.

9. The interface structure of claim 8, wherein the resin layer provides for K—Na ion exchange by facilitating charge delivery, and is comprised of sulfonated poly ether ether ketone (SPEEK) incorporated with micron-sized sulfonate styrene-crosslinked divinyl benzene-based cation exchange resin particles.

10. The interface structure of claim 9, wherein the piezoelectric composite layer free of carbon nanotubes comprises a matrix phase of piezo polymer present in the piezoelectric composite layer in a wt. % ranging from 10% to 30%, and a dispersed phase of piezo nanocrystal present throughout the matrix phase, and is present in the composite in a wt. % ranging from 70% to 90%.

11. The interface structure of claim 1, further comprising a dielectric polymer layer abutting the composite electrical impulse generating layer.

12. The interface structure of claim 1, wherein the interface structure has a three dimensional form factor selected from a group consisting a substantial sphere, a substantial sphere with projections, a sponge, a wire, a dendritic structure, paste and combinations thereof.

13. The interface structure of claim 1, wherein the piezo nanocrystal is a piezo ceramic material having crystals with a composition selected from a group consisting of lead zirconate ($PbZrO_3$), lead titanate ($PbTiO_3$), and combinations thereof.

14. The interface structure of claim 1, wherein the carbon nanotubes comprise single wall carbon nanotubes or multi-wall carbon nanotubes.

15. The interface structure of claim 1, wherein the at least one composite electrical impulse generating layer includes the piezo polymer present in a wt. % ranging from 10% to 99.9%.

16. The interface structure of claim 1, wherein the at least one composite electrical impulse generating layer includes the piezo nanocrystals present in a wt. % ranging from 15% to 99.9%.

17. The interface structure of claim 1, wherein the at least one composite electrical impulse generating layer includes the carbon nanotubes present in a wt. % ranging from 0.1 wt. % to 1.0 wt. %.

18. The interface structure of claim 1, wherein the piezo nanocrystals are a single crystal piezoelectric having the composition $(1-\chi)PbZn_{1/3}Nb_{2/3}O_{3-x}PbTiO_3$ (PZNT).

19. The interface structure of claim 1, wherein the piezo nanocrystals are of a composition selected from the group consisting of Li-doped $(K, Na)NbO_3$, $Ba(Ce_xTi_{1-\chi}O_3)$, and a combination thereof.

* * * * *